US010039508B2

(12) United States Patent
Abramovich et al.

(10) Patent No.: US 10,039,508 B2
(45) Date of Patent: Aug. 7, 2018

(54) ROLLING YOKE MOUNT FOR AN INTRA-ORAL 3D X-RAY SYSTEM

(71) Applicant: Sirona Dental, Inc., Long Island City, NY (US)

(72) Inventors: Mark Abramovich, Brooklyn, NY (US); Liang Hwang, Millstone, NJ (US); Aaron Bratslavsky, Brooklyn, NY (US); Steven Mita, Ossining, NY (US); Charles Smith, Brooklyn, NY (US)

(73) Assignee: Sirona Dental, Inc., Long Island City, NY (US)

( * ) Notice: Subject to any disclaimer, the term of this patent is extended or adjusted under 35 U.S.C. 154(b) by 370 days.

(21) Appl. No.: 14/672,595

(22) Filed: Mar. 30, 2015

(65) Prior Publication Data

US 2016/0287198 A1    Oct. 6, 2016

(51) Int. Cl.
*H05G 1/02* (2006.01)
*A61B 6/08* (2006.01)
*A61B 6/00* (2006.01)
*A61B 6/10* (2006.01)
(Continued)

(52) U.S. Cl.
CPC ............ *A61B 6/4476* (2013.01); *A61B 6/025* (2013.01); *A61B 6/105* (2013.01); *A61B 6/145* (2013.01); *A61B 6/4435* (2013.01); *A61B 6/4464* (2013.01)

(58) Field of Classification Search
CPC ......... A61B 6/025; A61B 6/105; A61B 6/145; A61B 6/4429; A61B 6/4435; A61B 6/4464; A61B 6/4476; A61B 6/447; A61B 6/4441; A61B 6/4482; A61B 6/04; A61B 6/06; A61B 6/4405; A61B 6/10; A61B 6/4028; A61B 6/02; A61B 6/032; A61B 6/0457; A61B 6/102; A61B 6/4458; A61B 6/583; A61B 6/584; A61N 5/103; A61N 5/1048; A61N 5/1081; G01T 1/2985; G01T 7/005;
(Continued)

(56) References Cited

U.S. PATENT DOCUMENTS 1,887,801 A * 11/1932 Cole ...................... G21K 1/025
248/123.11
2009/0180678 A1 * 7/2009 Kuduvalli ................ G06T 7/33
382/132
(Continued)

*Primary Examiner* — Irakli Kiknadze
(74) *Attorney, Agent, or Firm* — Fitzpatrick, Cella, Harper & Scinto

(57) ABSTRACT

An adjustable mount for positioning an x-ray source comprising a vertical member that can swivel around a yaw axis, a circular arc-shaped yoke having two ends and passing through the vertical member, a gantry attached to the two ends of the yoke, and an x-ray source attached to the gantry. The x-ray source can be rotated around the yaw axis by swiveling the vertical member, pitched around a pitch axis by pitching the gantry, and/or rotated around a roll axis by passing the yoke through the vertical member. A method for x-ray imaging that includes centering an x-ray source at an aiming position within an adjustable mount, and aiming the centered x-ray source at an x-ray sensor by rotating the x-ray source around a roll axis of the adjustable mount. An x-ray source mounting system comprising an x-ray source and an adjustable mount to which the x-ray source is attached.

16 Claims, 17 Drawing Sheets

(51) Int. Cl.
*A61B 6/14* (2006.01)
*A61B 6/02* (2006.01)

(58) Field of Classification Search
CPC . G06F 19/327; G06F 19/3437; G06F 19/3481
USPC ................................................ 378/193–198
See application file for complete search history.

(56) References Cited

U.S. PATENT DOCUMENTS

2010/0303205 A1* 12/2010 Kapoor ................ A61N 5/1048
378/65
2013/0129046 A1* 5/2013 Yamazaki ............... H01J 35/02
378/62

* cited by examiner

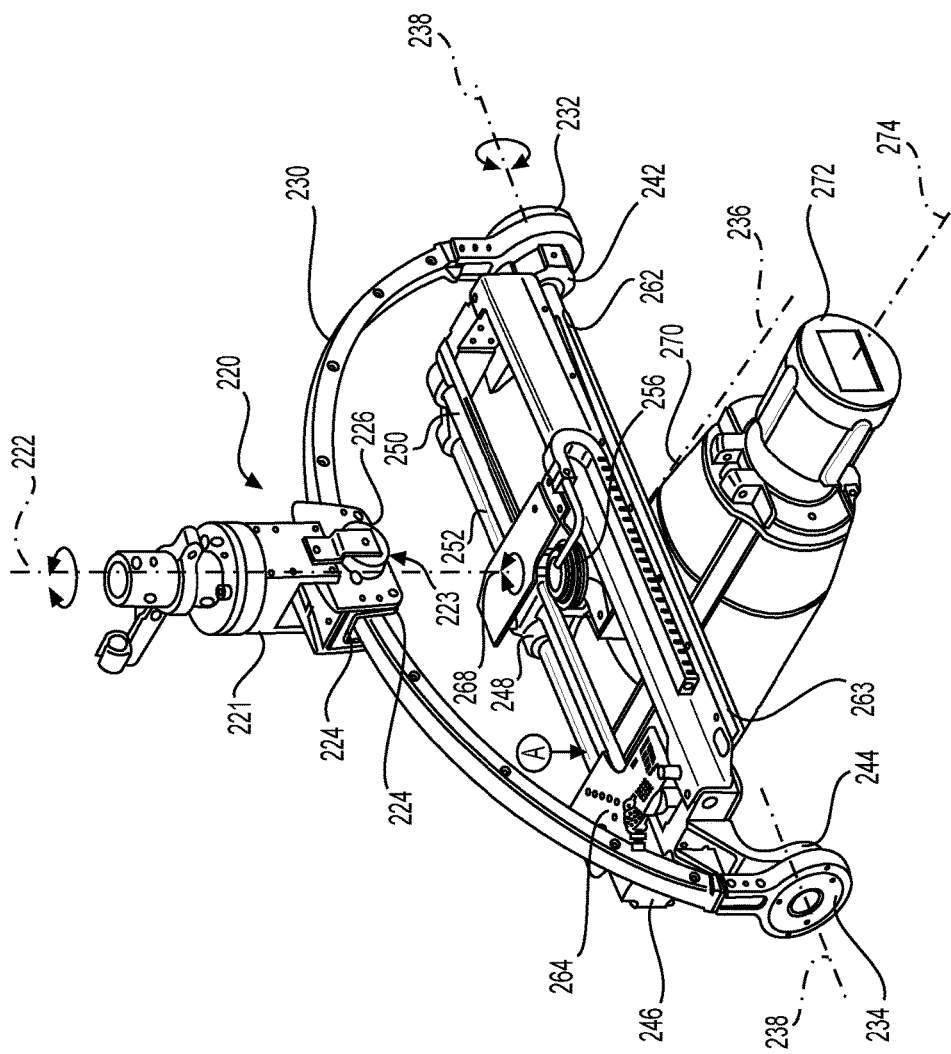

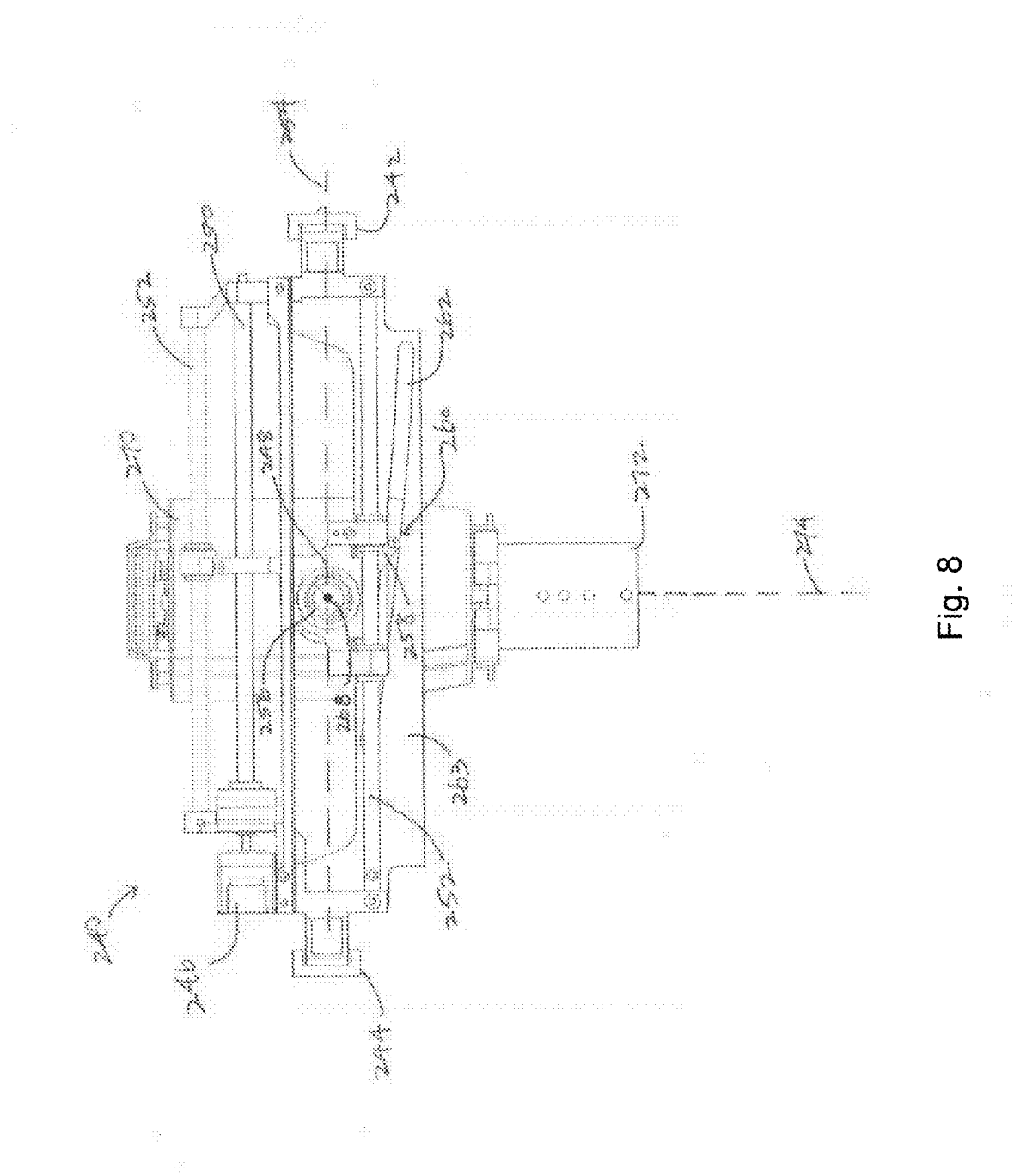

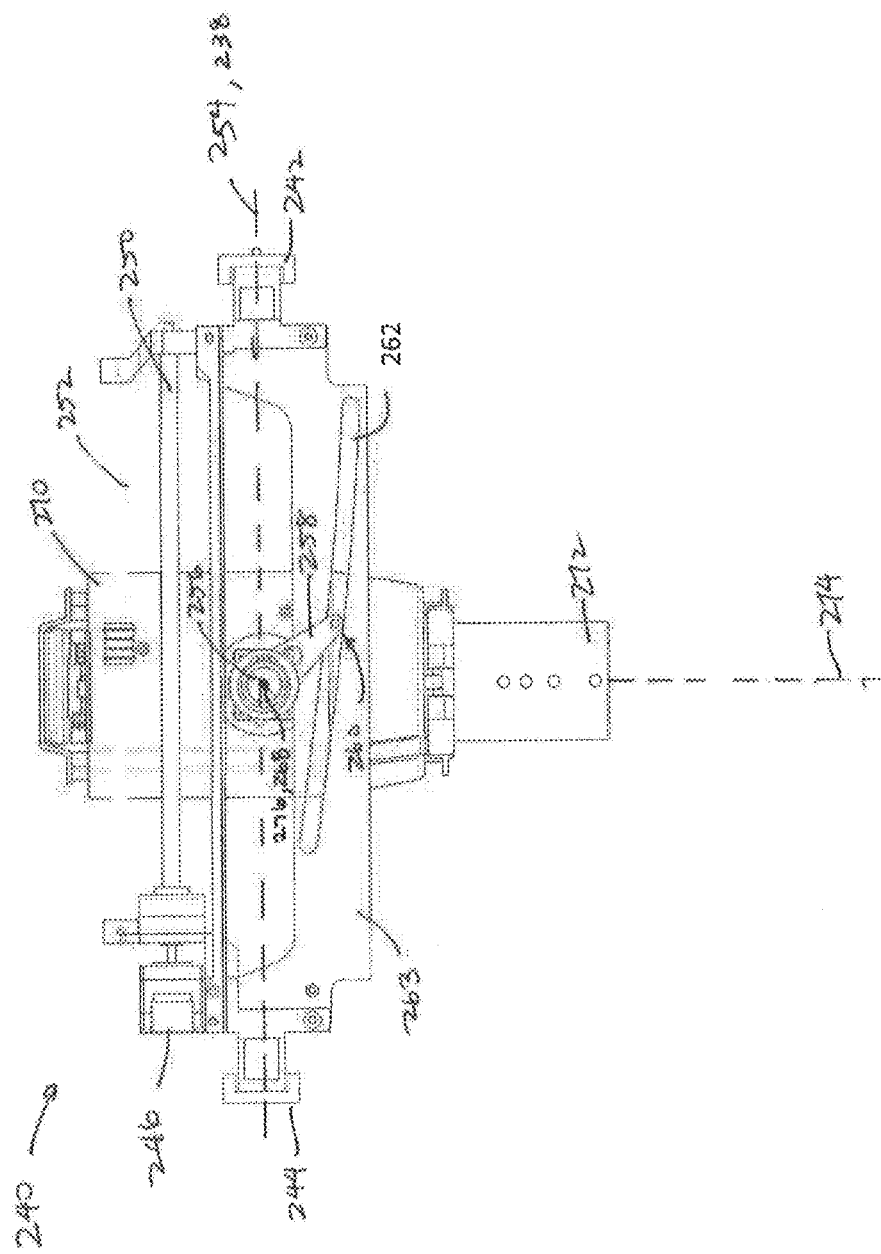

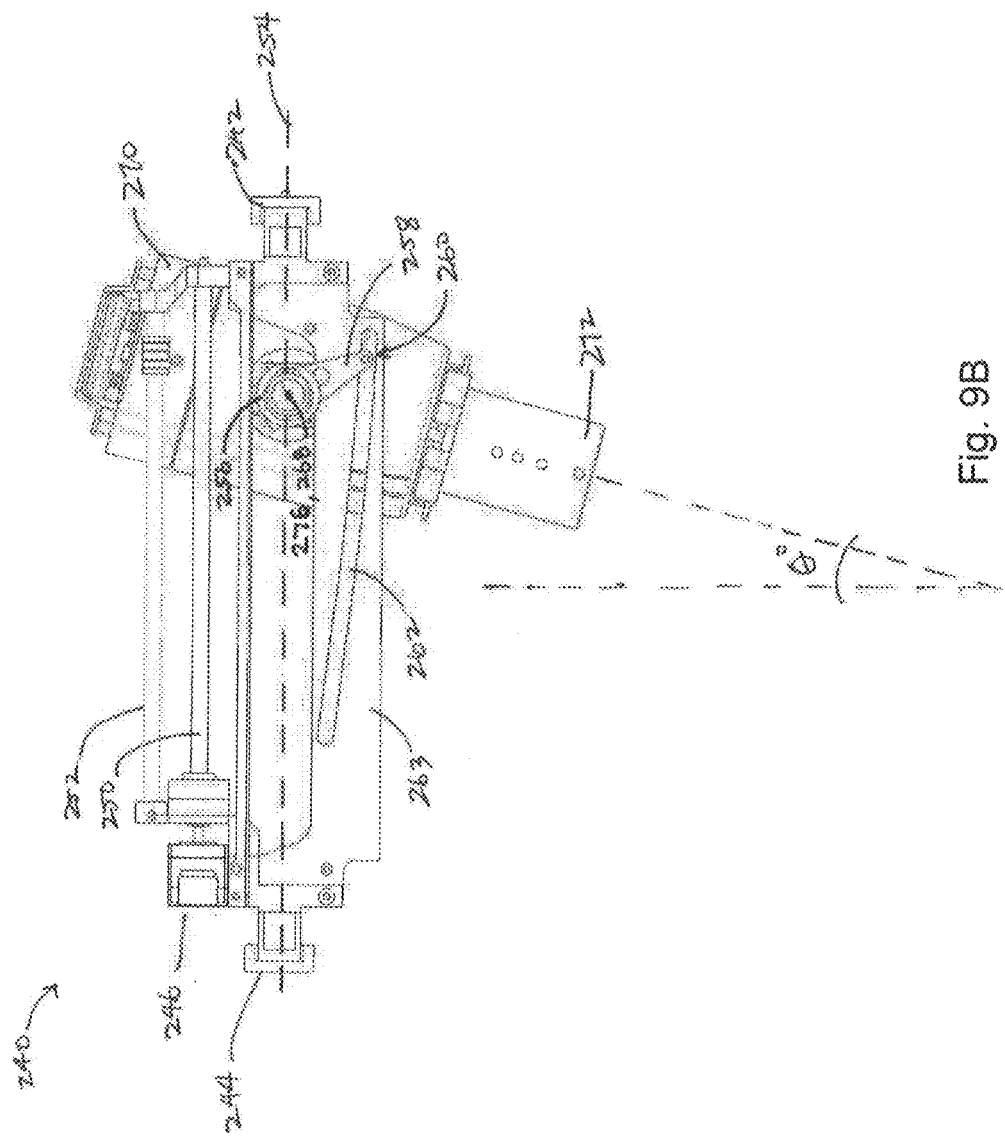

ROLLING YOKE MOUNT FOR AN INTRA-ORAL 3D X-RAY SYSTEM

BACKGROUND

Field of the Invention

The present application relates generally to an x-ray source mounting system, and, more particularly, to an adjustable and ergonomic motorized mounting system for sweeping an x-ray source to acquire an intraoral tomosynthesis dataset.

Description of Related Art

X-ray radiography can be performed by positioning an x-ray source on one side of an object (e.g., a patient) and causing the x-ray source to emit x-rays through the object toward an x-ray detector (e.g., radiographic film, a photostimulable phosphor plate, or a digital detector) located on the other side of the object. The x-ray source and detector remain substantially stationary during the radiography procedure. As the x-rays pass through the object, their energies are absorbed to varying degrees depending on the composition of the object, and x-rays arriving at the detector form a two-dimensional (2D) x-ray image (also known as a radiograph) based on the cumulative absorption through the object. Thus, a single radiograph does not provide sufficient depth information about features within an object. Features often appear to overlap in a conventional radiograph, although the features are separate in the object in three-dimensional (3D) space.

X-ray radiography can also be performed in dentistry, in which case, the object of interest to be imaged may be one or more dental anatomies of a patient. The patient typically sits in a reclinable dental chair, and an intraoral x-ray sensor, which can range in size, for example, from 20 mm×26 mm to 27 mm×37 mm, is placed in the patient's mouth adjacent to the dental anatomy of interest. To facilitate positioning of the x-ray source relative to the patient and the x-ray sensor, the x-ray source can be suspended from a wall-mounted or ceiling-mounted adjustable arm for translation in three-dimensional space (i.e., up, down, forward, backward, left, and right movement). The x-ray source housing can also can be designed to permit rotation of the x-ray source around a vertical axis (i.e., a yaw axis) and pivoting of the x-ray source around a horizontal axis (i.e., a pitch axis). However, dental radiographs are formed from cumulative absorption of X-rays (i.e., through the imaged dental anatomy), and do not provide sufficient depth information about the patient's dental anatomy.

X-ray computed tomography (CT) can provide depth information in a 3D image by rotating an x-ray source and detector 360° around an object. However, x-ray CT machines often are large, specialized equipment that require significant financial investments.

Tomosynthesis is an emerging imaging modality that provides 3D information about an object in the form of two-dimensional tomographic image slices by imaging the object with an x-ray source from multiple perspectives within a limited scan angle. Compared to CT imaging, tomosynthesis exposes patients to a lower x-ray dosage, acquires images faster, and can be less expensive. Tomosynthesis systems are commercially available for mammographic imaging. Tomosynthesis as an imaging modality can also be applied to intraoral imaging.

Although conventional dental radiography x-ray sources generally can be adjusted around a yaw axis and a pitch axis, they generally do not have the capability of being scanned through a limited scan angle so as to image an object from multiple perspectives for tomosynthesis imaging.

SUMMARY

Existing limitations associated with the foregoing, as well as other limitations, can be overcome by an adjustable mount for positioning an x-ray source, as well as an x-ray imaging system, an x-ray source mounting system, and a method for x-ray imaging that include an adjustable mount.

One embodiment described herein relates to an adjustable mount for positioning an x-ray source. The adjustable mount comprises a vertical member that can swivel around a yaw axis, a circular arc-shaped yoke having two ends and passing through the vertical member, wherein a pitch axis is defined through the two ends of the yoke and a roll axis is defined through the circle center of the yoke and orthogonally to a plane in which the yoke lies, a gantry attached to the two ends of the yoke, wherein the gantry is free to pitch about an axis defined through the two ends of the yoke, and an x-ray source attached to the gantry. In one aspect, the x-ray source can be rotated around the yaw axis by swiveling the vertical member, pitched around the pitch axis by pitching the gantry, and/or rotated around the roll axis by passing the yoke through the vertical member. In another aspect, the gantry includes a motorized translation stage, and the x-ray source is attached to the gantry by way of the translation stage. In yet another aspect, the gantry includes a cam channel that rotates the x-ray source based on a translation of the x-ray source by the translation stage. In another aspect, the vertical member includes bearings on which the yoke rolls and a brake to clamp the yoke.

Another embodiment described herein relates to an x-ray imaging system. The x-ray imaging system comprises an adjustable mount that includes a vertical member that can swivel around a yaw axis, a circular arc-shaped yoke having two ends and passing through the vertical member, wherein a pitch axis is defined through the two ends of the yoke and a roll axis is defined through the circle center of the yoke and orthogonally to a plane in which the yoke lies, and a gantry attached to the two ends of the yoke, wherein the gantry is free to pitch about an axis defined through the two ends of the yoke. The x-ray imaging system further includes an x-ray source attached to the gantry of the adjustable mount, and an x-ray sensor. In one aspect, the x-ray source can be aimed at the x-ray sensor by rotating around the yaw axis by swiveling the vertical member, pitching around the pitch axis by pitching the gantry, and/or rotating around the roll axis by passing the yoke through the vertical member.

Another embodiment described herein relates to a method for x-ray imaging with an x-ray imaging system that includes an x-ray sensor and an x-ray source attached to an adjustable mount, the adjustable mount permitting rotation of the x-ray source around a yaw axis, a pitch axis, and a roll axis. The method comprises centering an x-ray source at an aiming position within an adjustable mount, and aiming the centered x-ray source at an x-ray sensor by rotating the x-ray source around a roll axis of the adjustable mount. In one aspect, the aiming of the x-ray source at the x-ray sensor further includes rotating the x-ray source around at least one of a yaw axis of the adjustable mount and a pitch axis of the adjustable mount. In another aspect, the method further includes scanning the aimed x-ray source through a predetermined scan angle, causing the x-ray source to emit x-rays during the scanning, and detecting the emitted x-rays at the x-ray sensor.

Yet another embodiment described herein relates to an x-ray source mounting system. The x-ray source mounting system comprises an x-ray source, and an adjustable mount to which the x-ray source is attached, the adjustable mount configured to provide the x-ray source with rotational degrees of freedom around a yaw axis, a pitch axis, and a roll axis. In one aspect, a center of mass of the x-ray source does not shift when the x-ray source is rotated around at least one of a yaw axis, a pitch axis, and a roll axis.

Further features and advantages, as well as the structure and operation of various embodiments herein, are described in detail below with reference to the accompanying drawings.

BRIEF DESCRIPTION OF THE DRAWINGS

Tomosynthesis System

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 3D is a front-top-right perspective view of subcomponents of the x-ray source mounting system illustrated in FIG. 2, with housing covers removed, according to an example embodiment herein.

FIG. 8 is a top view of a translation gantry subassembly and an x-ray source with the components illustrated in FIG. 3A, according to an example embodiment herein.

FIG. 9A is a top view of a translation gantry subassembly and an x-ray source with the components illustrated in FIG. 3A, according to an example embodiment herein, wherein the translation gantry subassembly and the x-ray source are configured in an aiming position.

FIG. 9B illustrates another position of the translation gantry subassembly and the x-ray source illustrated in FIG. 9A, according to an example embodiment herein.

Figure 1:
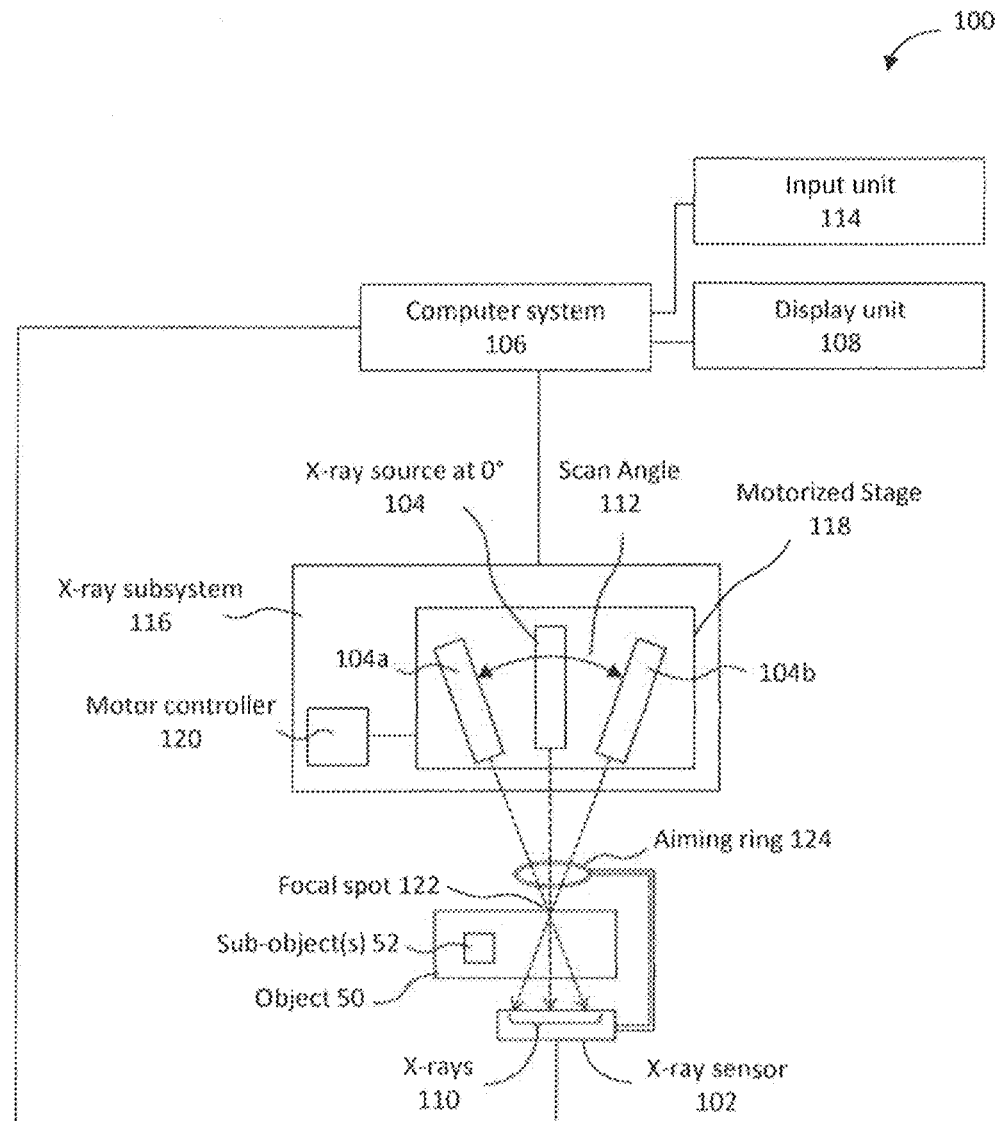
FIG. 1 is a system block diagram of a tomosynthesis system according to an example embodiment herein.

Different ones of the Figures may have at least some reference numerals that are the same in order to identify the same components, although a detailed description of each such component may not be provided below with respect to each Figure.

DETAILED DESCRIPTION OF THE PREFERRED EMBODIMENTS

In accordance with example aspects described herein, FIG. 1 illustrates a block diagram of an intraoral tomosynthesis system 100 for obtaining an intraoral tomosynthesis dataset.

The system 100 can be operated to obtain one or more x-ray images of an object 50 of interest, which may further include one or more sub-object(s) 52. For example, object 50 may be a dental anatomy of a patient. More particularly, object 50 may be a tooth (or teeth) and surrounding dentition of the patient, and sub-object(s) 52 may be root structures within the tooth, for example.

The system 100 includes an x-ray sensor 102 and an x-ray source subsystem 116, both of which, including subcomponents thereof, are electrically coupled to a computer system 106. In one example, the x-ray source subsystem 116 hangs from a ceiling- or wall-mounted adjustable arm (see FIG. 2, discussed further herein below), so as to be freely positioned relative to an object 50. The x-ray source subsystem 116 further includes an x-ray source 104 mounted on a motorized stage 118 and also shows an on-board controller 120. The on-board controller 120 can control, among other things, the motion of the motorized stage 118.

The computer system 106 is electrically coupled to a display unit 108 and an input unit 114. The display unit 108 can be an output and/or an input user interface.

The x-ray sensor 102 is positioned on one side of the object 50 and a receiving surface of the x-ray sensor 102 extends in an x-y plane in a Cartesian coordinate system. The x-ray sensor 102 can be, for example, a complementary metal-oxide semiconductor (CMOS) digital detector array of pixels, a charge-coupled device (CCD) digital detector array of pixels, or the like. In an example embodiment herein, the size of the x-ray sensor 102 varies according to the type of patient to whom object 50 belongs, and more particularly, the x-ray sensor 102 may be one of a standard sized, rectangular intraoral sensor employed in the dental industry. Examples of the standard dental sizes include a "Size-2" sensor, which is approximately 27×37 mm in size and is typically used on adult patients, a "Size-1" sensor, which is approximately 21×31 mm in size and is typically used on patients that are smaller than Size-2 adult patients, and a "Size-0" sensor, which is approximately 20×26 mm in size and is typically used on pediatric patients. In a further example embodiment herein, each pixel of the x-ray sensor 102 has a pixel width of 15 μm, and correspondingly, the Size-2 sensor has approximately 4 million pixels in a 1700×2400 pixel array, the Size-1 sensor has approximately 2.7 million pixels in a 1300×2000 pixel array, and the Size-0 sensor has approximately 1.9 million pixels in a 1200×1600 pixel array. The color resolution of the x-ray sensor 102 may be, in one example embodiment herein, a 12-bit grayscale resolution, although this example is not limiting, and other example color resolutions may include an 8-bit grayscale resolution, a 14-bit grayscale resolution, and a 16-bit grayscale resolution.

The x-ray source 104 is positioned on an opposite side of the object 50 from the x-ray sensor 102. The x-ray source 104 emits x-rays 110 which pass through object 50 and are detected by the x-ray sensor 102. The x-ray source 104 is oriented so as to emit x-rays 110 towards the receiving surface of the x-ray sensor 102 in at least a z-axis direction of the Cartesian coordinate system, where the z-axis is orthogonal to the x-y plane associated with the receiving surface of the x-ray sensor 102.

The x-ray source 104 can also emit x-rays 110 while positioned at each of multiple different locations within a scan angle 112, where a 0° position in the scan angle 112 corresponds to the position for emitting x-rays 110 along the z-axis. In one example embodiment herein, the user initially positions the x-ray source subsystem 116, and hence, also the x-ray source 104, to a predetermined starting position relative to the object 50. The computer system 106 then controls the on-board controller 120 to move the x-ray source 104 via the motorized stage 118, based on the known starting position, to sweep through each of the different locations within the scan angle 112. The sweep of the x-ray source 104 through the scan angle 112 can be performed as a continuous motion or as discrete steps. The computer system 106 controls the x-ray source 104 to cause the source 104 to emit x-rays 110 at each of those locations.

In FIG. 1, the 0° position is represented in x-ray source 104, while reference numerals 104a and 104b represent the same x-ray source but in two other example positions within the scan angle 112. The scan angle 112 can be, for example, ±20° from the 0° position, although this example is not limiting. For example, in other embodiments, the source 104 can be positioned to emit x-rays 110 in any desired direction, and not necessarily only in a plane, direction, or angle as described in the examples above.

As emitted x-rays 110 pass through the object 50, photons of x-rays 110 will be more highly attenuated by high density structures of the object 50, such as calcium-rich teeth and bone, and less attenuated by soft tissues, such as gum and cheek. One or more of the attenuating structures can be represented by sub-object(s) 52. X-rays 110 passing through and attenuated by object 50, are projected onto x-ray sensor 102, which converts the x-rays 110 into electrical signals and provides the electrical signals to computer system 106. In one example embodiment, the x-ray sensor 102 may be an indirect type of sensor (e.g., a scintillator x-ray detector) that first converts x-rays 110 into an optical image and then converts the optical image into the electrical signals, and in another example embodiment, the x-ray sensor 102 may be a direct type of sensor (e.g., a semiconductor x-ray detector) that converts x-rays 110 directly into the electrical signals. The computer system 106 processes the electrical signals to form a two-dimensional projection image of the object 50 in a known manner. In one example embodiment herein, the image size of the two-dimensional projection image corresponds to the dimensions and the number of pixels of the x-ray sensor 102.

It may be deemed important to aim the x-ray source 104 relative to the x-ray sensor 102 such that the full receiving surface of the x-ray sensor 102 is exposed to x-rays 110 emitted by the x-ray source 104 as the x-ray source 104 is swept through each position of the scan angle 112. If the x-ray source 104 is not properly aimed, a part of the x-ray sensor 102 may be left unexposed to x-rays 110 at one or more positions of the x-ray source 104 in the scan angle 112, and the corresponding acquired projection image(s) will appear clear (i.e., white) and devoid of sub-object(s) 52 in the unexposed region. This error is known as a cone cut. The x-ray source 104 may be aimed via an x-ray mounting system according to an example embodiment described further below (i.e., as described with reference to at least FIG. 2), such that, when the x-ray source 104 is at the 0° position, the emitted x-rays 110 are aimed at the center of the x-ray sensor 102 and also are substantially orthogonal to the x-ray sensor 102. In at least some example embodiments herein, an extraoral aiming ring 124 is attached to x-ray sensor 102 to provide a target to facilitate aiming of the x-ray source 104. Additionally, the aiming of the x-ray source 104 may cause the x-rays 110 emitted during the sweep of scan angle 112 to converge substantially at a focal spot 122, where the focal spot 122 may be, for example, located close to the sensor 102.

The system 100 can collect a plurality of projection images, in the manner described above, by first positioning the x-ray source 104 at different angles, including at least the 0° position, and emitting x-rays 110 at each of those different angles through object 50 towards x-ray sensor 102. For example, the plurality of projection images may include a total of fifty-one projections: one orthogonal projection image, obtained when the x-ray source is at the 0° position, and fifty projection images, each obtained when the x-ray source 104 is positioned at different angles within a range of ±20° from the z-axis (corresponding to the scan angle 112). In other example embodiments, the number of projection images may range from twenty-five to seventy. Because the orthogonal projection image is obtained when the x-ray source is at the 0° position, the orthogonal projection image has the same appearance as a conventional x-ray image. That is, the two-dimensional orthogonal projection image has no depth perception, and one or more sub-object(s) 52 within object 50 may appear overlaid one on top of another in the orthogonal projection image. On the other hand, sub-object(s) 52 at different depths of the z-axis within object 50 undergo varying degrees of parallax when imaged from different angles along the scan angle 112.

The computer system 106 processes the plurality of projection images to reconstruct a series of two-dimensional tomosynthesis image slices, according to any existing or later developed reconstruction technique. In one example embodiment, herein, reconstruction of the tomosynthesis image slices utilizes a shift-and-add technique, such as that described in the publication by D. G. Grant, entitled "Tomosynthesis: A Three-Dimensional Radiographic Imaging Technique", IEEE Transactions on Biomedical Engineering, Volume 19, 1972, pp. 20-28, and also described in the review publication by J. T. Dobbins et al., entitled "Digital X-ray Tomosynthesis: Current State of the Art and Clinical Potential", Physics in Medicine and Biology, Volume 48, 2003, pp. R65-R106 (the J. T. Dobbins et al. publication), which are incorporated by reference herein in their entireties, as if set forth fully herein.

X-Ray Source Mounting System

Figure 2:
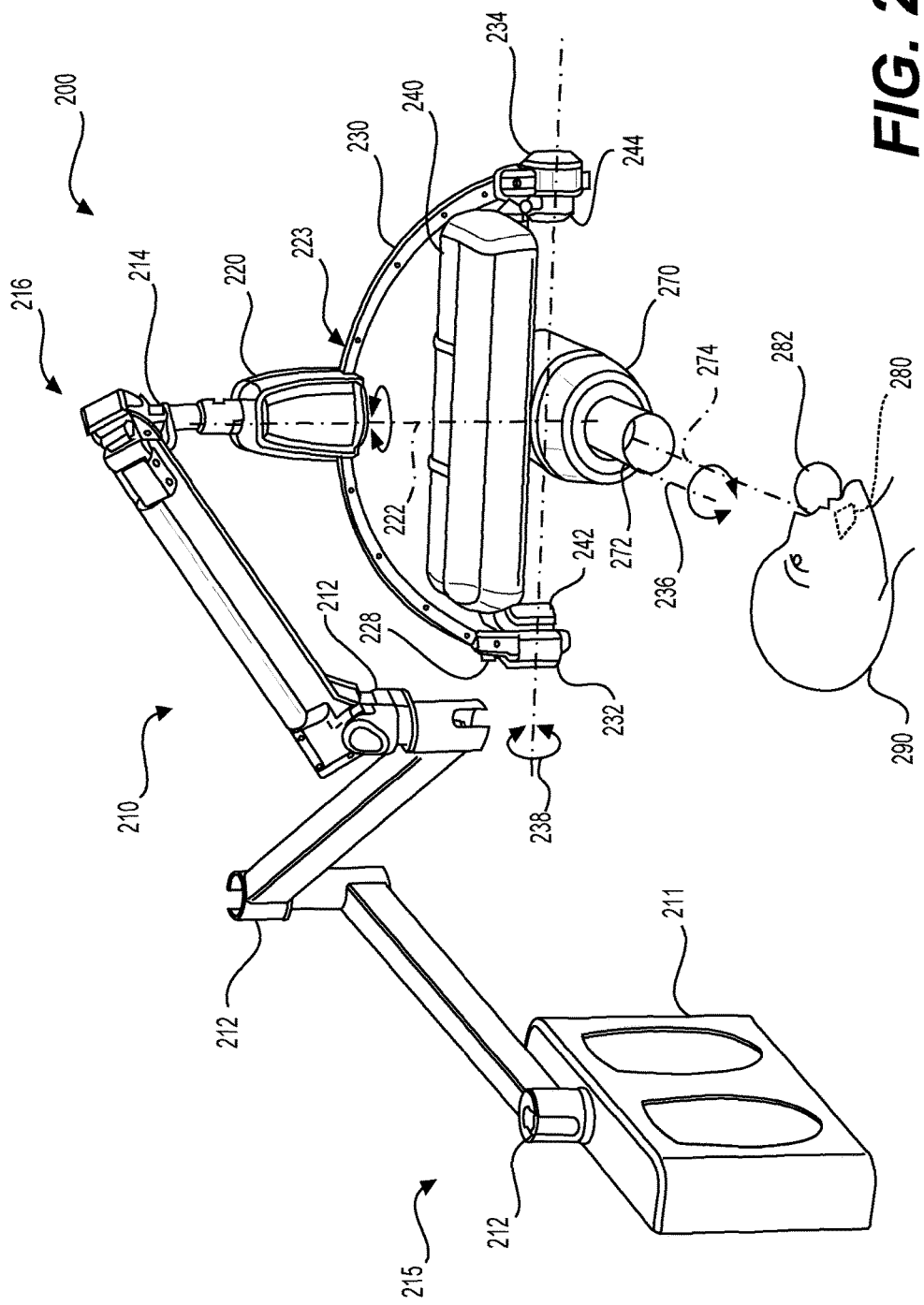
FIG. 2 illustrates an x-ray source mounting system according to an example embodiment herein.

Having generally described a system 100 for obtaining a tomosynthesis dataset, embodiments of an adjustable mounting system 200, which includes an adjustable arm 210, a vertical member 220 suspended from the adjustable arm 210, a yoke 230 that can be angularly displaced through the vertical member 220, a translation gantry 240 attached to the yoke 230, and an x-ray source 270 attached to the translation gantry 240, will now be described in conjunction with FIGS. 2, 3A-3D, and 4-7. In particular, FIG. 2 illustrates an example embodiment of a mounting system 200, and FIGS. 3A-3D and 4-7 are different views of that mounting system 200, with housing covers removed, so as to show underlying subcomponents. FIGS. 3A-3D and 4-7 provide differing perspective views of the mounting system 200 for the purposes of clarity. Additionally, FIGS. 3B and 3C illustrate the subcomponents shown in FIG. 3A, with the x-ray source 270 translated to different positions than the position shown in FIG. 3A, as will be described further herein below.

The exemplary mounting system 200 and x-ray source 270 shown in FIG. 2 can collectively serve as the x-ray source subsystem 116 illustrated in FIG. 1, and more particularly, the x-ray source 270 of FIG. 2 can serve as the x-ray source 104 illustrated in FIG. 1. Together with at least some of the other components illustrated in FIG. 1, the mounting system 200 and the x-ray source 270 also can be useful for performing tomosynthesis imaging, that is, for acquiring a plurality of projection images at different angles along a scan angle. The foregoing components and their interconnection will now be discussed in greater detail.

One end 215 of the adjustable arm 210 illustrated in FIG. 2 can be mounted to a stationary structure, such as a wall or a ceiling. In one example embodiment, the adjustable arm 210 can be mounted to a wall by a mounting panel 211, which, in a further example embodiment herein, can also include controls (not shown) for adjusting exposure settings of the x-ray source 270.

As shown in FIG. 2, the vertical member 220 (and by extension, the yoke 230, the translation gantry 240, and the x-ray source 270, attached thereto) is suspended from another end 216 of the adjustable arm 210 (i.e., the end of the adjustable arm 210 not mounted to a stationary structure). The adjustable arm 210 can be segmented and can include one or more joints 212 (e.g., a hinge, a swivel, a universal joint, or the like) so as to allow free translation of the x-ray source 270 in three-dimensional space, that is, in the up, down, left, right, forward, and backward directions.

In an example embodiment herein, the vertical member 220 is suspended vertically from one end 216 of the adjustable arm 210 by a joint 214, such that the vertical member 220 defines a vertically-oriented yaw axis 222, regardless of the position and orientation of the adjustable arm 210. Additionally, the vertical member 220 includes a rotation mechanism, such as a swivel 221 (illustrated in FIGS. 3A-3D and 4-7), that allows the vertical member 220 (and by extension, the yoke 230, the translation gantry 240, and the x-ray source 270 attached thereto) to rotate freely around the yaw axis 222, independent of the position and orientation of the adjustable arm 210. For example, the vertical member 220 can rotate at any angle within at least 360° around the yaw axis.

Subcomponents of the vertical member 220 according to an example embodiment herein will now be discussed, with reference to FIGS. 3A-3D and 4-7, which show the vertical member 220 and the translation gantry 240 with their respective housing covers removed. As illustrated in FIGS. 3A-3D and 4-7, the vertical member 220 includes a bearing assembly 223, which acts as a channel through the vertical member 220. The yoke 230 is movably constrained to the channel of the bearing assembly 223, and can be angularly displaced through the bearing assembly 223 and thus through the vertical member 220. In one example embodiment herein, the bearing assembly 223 includes at least one roller bearing 224 upon which the yoke 230 rolls as it is angularly displaced through the vertical member 230. In other example embodiments herein, the bearing assembly can include other types of bearings, such as ball bearings, low-friction solid bearings, and the like, or any component otherwise suitable to facilitate low-resistance movement of the yoke 230 through the bearing assembly 223.

The vertical member 220 also includes at least one brake 226. In one example embodiment, the brake 226 can comprise two electromechanical brakes, which apply a clamping force to the yoke 230. In a default state, the brake 226 holds the yoke 230 in place and substantially prevents any motion of the yoke 230 through the bearing assembly 223, and can lock the position of the yoke 230 relative to the vertical member 220. A brake-release button 228 (shown on FIG. 2) is provided on the mounting system 200 and is in communication with the brake 226. While the brake-release button 228 is depressed, the brake 226 is controlled to release the yoke 230, which can then freely pass through the bearing assembly 223 in the manner described above.

The yoke 230 is formed in a circular arc shape and includes two ends 232 and 234. More particularly, in one example embodiment herein, the yoke 230 is semicircular in shape. A roll axis 236 is defined in relation to the yoke 230 as an axis passing through the circle center of the yoke 230 and being orthogonal to the plane in which the yoke 230 lies. The roll axis 236 is also orthogonal to the yaw axis 222. Accordingly, the act of angularly displacing the semicircular yoke 230 through the vertical member 220 can also be described in other words as rotating the yoke 230 around the roll axis 236. In an example embodiment herein, the yoke 230 is restricted by the vertical member 220 to a single degree of freedom, namely, the rotating of the yoke 230 around the roll axis 236, and the yoke 230 can be rotated around the roll axis 236 up to 180°.

In other example embodiments herein, the yoke 230 can be formed in other curved arc shapes.

The brake-release button 228 (FIG. 2) can be located at a convenient location, such as, for example, at one end 232 or 234 of the yoke 230, such that an operator can single-handedly depress the brake-release button 228 to control the brake 226 to release the yoke 230, hold the yoke 230 by the end 232 or 234 where the button 228 is located, and rotate the yoke 230 through the vertical member 220.

The translation gantry 240 is attached between the yoke ends 232 and 234, as shown in FIGS. 3A-3D and 4-7. The translation gantry 240 can include arms 242 and 244 which are movably attached to the yoke ends 232 and 234, respectively, each point of attachment forming a pivot such that the translation gantry 240 can be pitched about a pitch axis 238 substantially defined through the yoke ends 232 and 234 and substantially orthogonal to the roll axis 236. In one example embodiment, the translation gantry 240 can be pitched about the pitch axis 238 in a range of about ±45°. In a further example embodiment herein, the pitch axis 238 intersects the circle center of the yoke 230, and thus also intersects the roll axis 236. In a further example embodiment, the yaw axis 222, the roll axis 236, and the pitch axis 238 intersect or are substantially close to intersecting each other at the circle center of the yoke 230.

In one example embodiment herein, the yoke ends 232 and 234 and the translation gantry arms 242 and 244 are stationary relative to one another while at rest, by virtue of the balance of the translational gantry 240 (as will be described further herein below) and/or the static frictional forces between each yoke end 232 and 234 and the corresponding arm 242 and 244. Thus, the translation gantry 240 is pitched by applying a rotational force thereto that overcomes the static frictional forces at the points of attachment. In one example embodiment herein, the yoke ends 232 and 234 are cylindrical clamping collars that receive complementary-shaped shaft parts of the arms 242 and 244 of the translation gantry 240. Alternatively, arms 242 and 244 may include cylindrical clamping collars that receive complementary-shaped shaft parts of the yoke ends 232 and 234.

Subcomponents of the translation gantry 240 according to an example embodiment herein will now be described, with reference to FIGS. 3A-3D and 4-7, which show the vertical member 220 and the translation gantry 240 of FIG. 2 with their respective housing covers removed, and at least some of the figures provide different perspective views for the purposes of clarity. The translation gantry 240 houses a motor 246, a translation stage 248, a linkage 250 attached to both the motor 246 and the translation stage 248, and one or more linear guide(s) 252 on which the translation stage 248 rides. In one example embodiment herein, the linkage 250 converts a rotational motion of the motor 246 into a linear motion of the translation stage 248, and, in a further example embodiment herein, the linkage 250 can be a lead screw. The linkage 250 and the linear guide(s) 252 are aligned in a direction substantially parallel to the pitch axis 238, so that the translation stage 248 is translated along a translation axis 254 (see, e.g., FIGS. 8 and 9A-C) that also is substantially parallel to the pitch axis 238.

A shaft 256 is rotatably disposed through the translation stage 248, and an axis of rotation 268 of the shaft 256 is orthogonal to the translation axis 254. In particular, in one example embodiment herein, the shaft 256 is substantially cylindrical in shape, and the axis of rotation 268 is coincidental with a cylindrical axis of the cylindrically-shaped shaft 256. The x-ray source 270 attaches to the translation gantry 240 by way of the shaft 256.

Figure 9C:
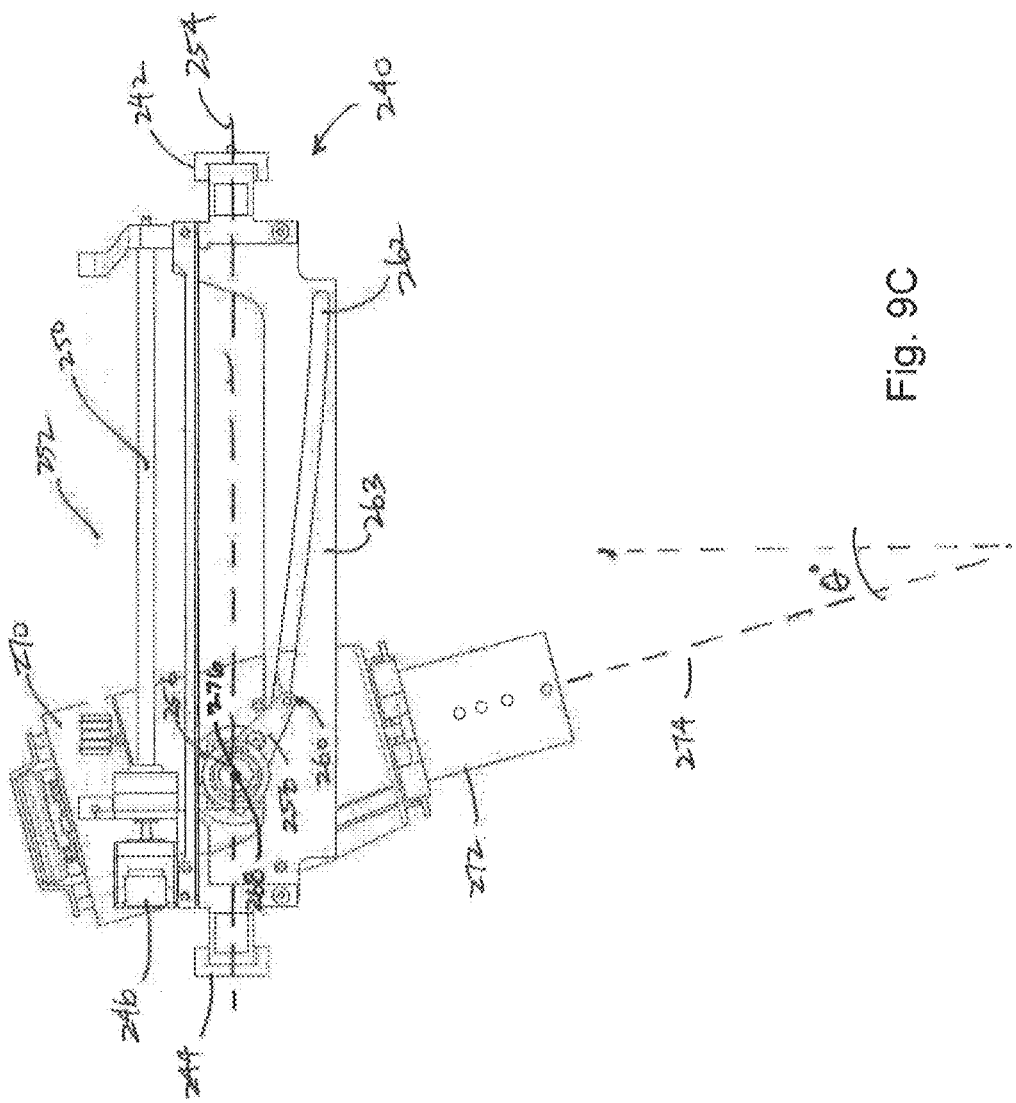
FIG. 9C illustrates another position of the translation gantry subassembly and the x-ray source illustrated in FIG. 9A, according to an example embodiment herein.

FIGS. 8 and 9A-9C will now be discussed. FIGS. 8 and 9A-9C are top views of the translation gantry 240 and x-ray source 270 (that is, on FIGS. 3D and 4-6, from a view point of "A" looking towards the translation gantry 240) according to an example embodiment herein. FIG. 9A illustrates the same translation gantry 240 shown in FIG. 8, except that the translation stage 248 has been removed from view in FIG. 9A to show underlying features, including the shaft 256, an arm 258, and a guide pin 260. FIGS. 9B and 9C each illustrate the same components of FIG. 9A (i.e., the translation gantry 240 and x-ray source 270), but with the x-ray source 270 at different locations along the translation axis 254 and with different rotations, by virtue of a cam system included in the translation gantry 240, which will now be described in greater detail with reference to FIGS. 8 and 9A-9C (although parts of the cam system are visible in other ones of FIGS. 3A-3D and 4-7).

In the example embodiment illustrated in FIGS. 8 and 9A-9C, the translation gantry 240 includes a cam system comprising a cam channel 262 disposed in a cam plate 263 of the translation gantry 240, and the arm 258 secured at its first end to the shaft 256 and constrained at its second end within the cam channel 262 by way of the guide pin 260.

As shown in FIGS. 8 and 9A-9C, the cam channel 262 is angled relative to the translation axis 254. As the translation stage 248 (shown in FIG. 8) is translated on the linkage 250 and guide(s) 252 along the translation axis 254 by motor 246, the guide pin 260 of the arm 258 follows along in the cam channel 262. For example, in FIG. 9B, the shaft 256 and x-ray source 270 have been translated by motor 246 (by virtue of being attached to the translation stage 248 (not shown in FIG. 9B)) to the end of the linkage 250 that is closer to translation gantry arm 242, and the guide pin 260 correspondingly has followed along to the end of the cam channel 262 that is closer to the translation gantry arm 242, by virtue of the guide pin 260 being connected to the shaft 256 via arm 258. Similarly, in FIG. 9C, the shaft 256 and x-ray source 270 have been translated by motor 246 (by virtue of being attached to the translation stage 248 (not shown in FIG. 9C)) to the end of the linkage 250 that is closer to translation gantry arm 244, and the guide pin 260 correspondingly has followed along to the end of the cam channel 262 that is closer to the translation gantry arm 244, by virtue of the guide pin 260 being connected to the shaft 256 via arm 258. FIG. 9A shows the shaft 256 and the x-ray source 270 translated (by way of motor 246 translating the translation stage 248 (not shown in FIG. 9A)) to a position midway between their positions shown respectively in FIGS. 9B and 9C, and FIG. 9A also shows the guide pin 260 at a midway position in the cam channel 262.

As can be understood from FIGS. 9A-9C, the translation of the translation stage 248 (shown in FIG. 8) and the shaft 256 by motor 246 from one end of the linkage 250 (e.g., as shown in FIG. 9B) to the other end of the linkage 250 (e.g., as shown in FIG. 9C) simultaneously imparts a rotation to the shaft 256, because the guide pin 260 is constrained to the angled cam channel 262 as it follows the translation of the translation stage 248 in the manner described above. (The translation and rotation of the x-ray source illustrated in each of FIGS. 9A-9C correspond to the translation and rotation of the x-ray source illustrated in each of the perspective views of FIGS. 3A-3C, respectively.)

In one example embodiment, the translation stage 248 (and by extension, the shaft 256 and the x-ray source 270) can be translated up to a total distance of 10 inches (254 mm). To convert that total translation distance of 10 inches (254 mm) into a total rotation of 40° of the shaft 256, the cam channel 262 is along a gradual spline with an angle approximately 4.8-8.5° relative to the translation axis 254, and the arm 258 is approximately 2 inches (51 mm) in length. It will be understood that the translation described above can be for any amount up to an end-to-end translation on the linkage 250, and the degree of rotation of the shaft 256 will be commensurate with that amount of translation.

In one example embodiment herein, the cam plate 263 forms a fixed, integral part of the structure of the translation gantry 240. In another example embodiment herein, the cam plate 263 is interchangeable and can be removably affixed in the translation gantry. Each of a plurality of interchangeable cam plates can be used that have a different cam channel design (e.g., different angles that achieve different rotations of the shaft 256).

Figure 3A:
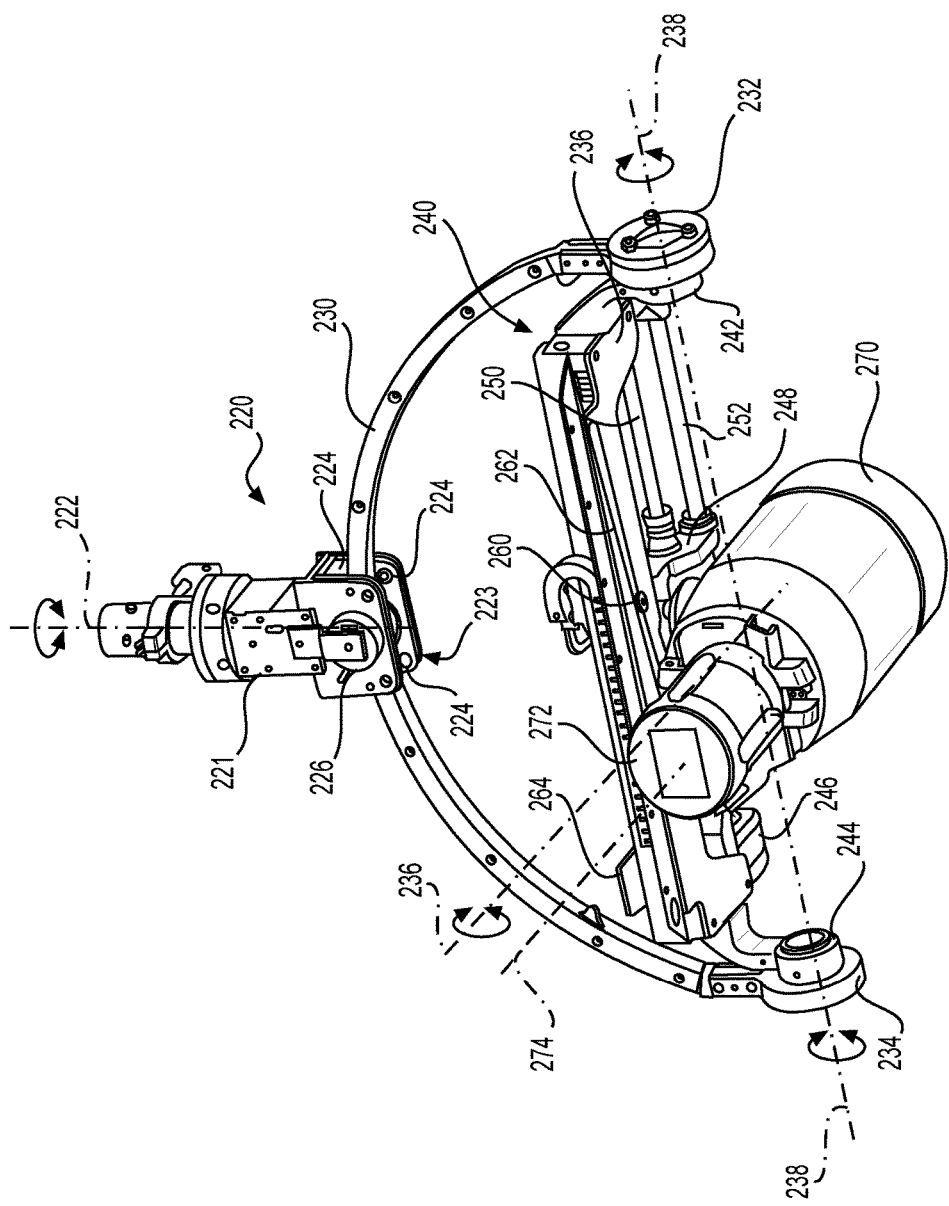
FIG. 3A is a front-bottom-left perspective view of subcomponents of the x-ray source mounting system illustrated in FIG. 2, with housing covers removed, according to an example embodiment herein.
Figure 3B:
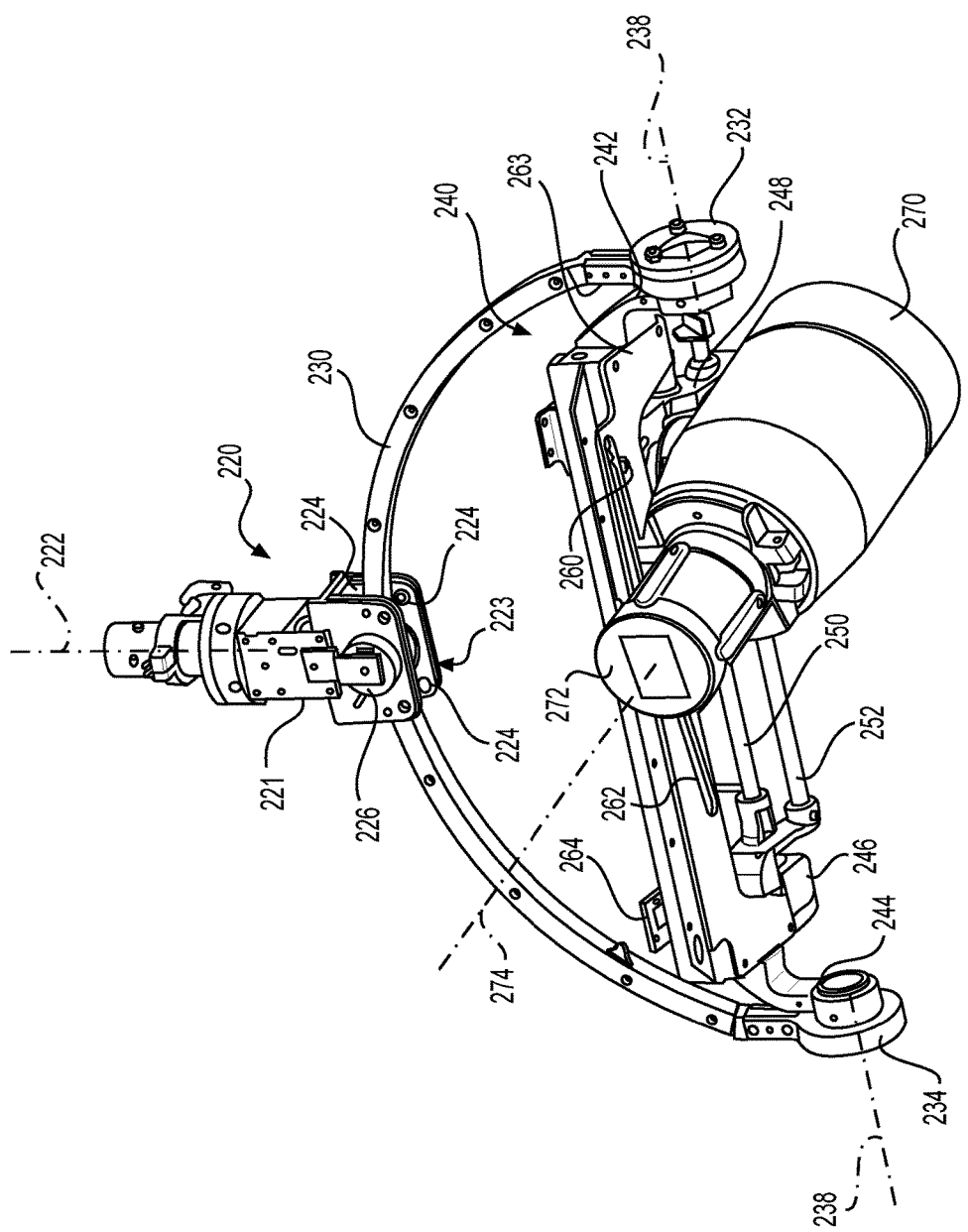
FIG. 3B is a front-bottom-left perspective view of the subcomponents of the x-ray source mounting system illustrated in FIG. 3A, in a case where the x-ray source is in a different position than that in FIG. 3A.
Figure 3C:
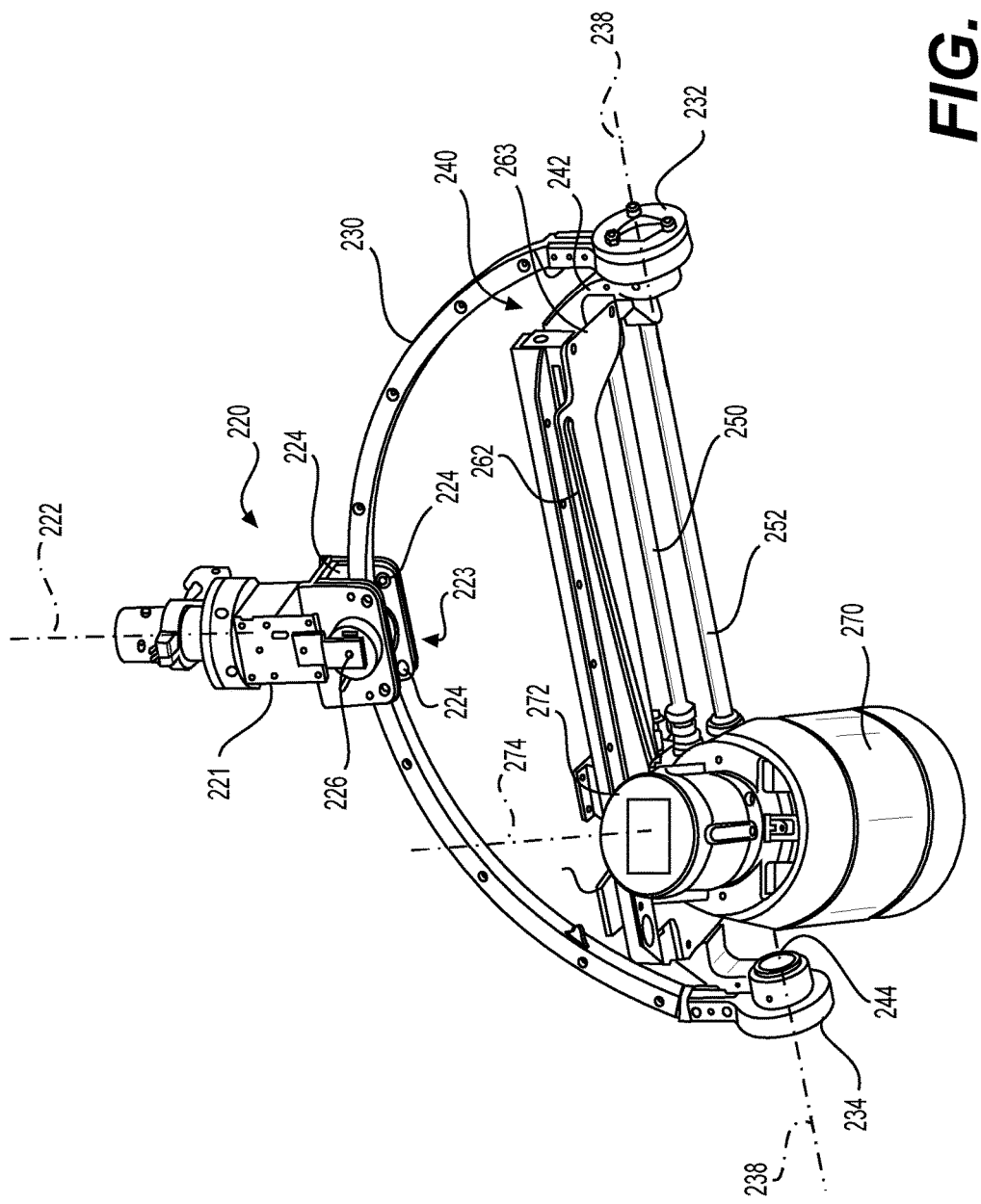
FIG. 3C is a front-bottom-left perspective view of the subcomponents of the x-ray source mounting system illustrated in FIG. 3A, in a case where the x-ray source is in a different position than that in FIGS. 3A and 3B.
Figure 4:
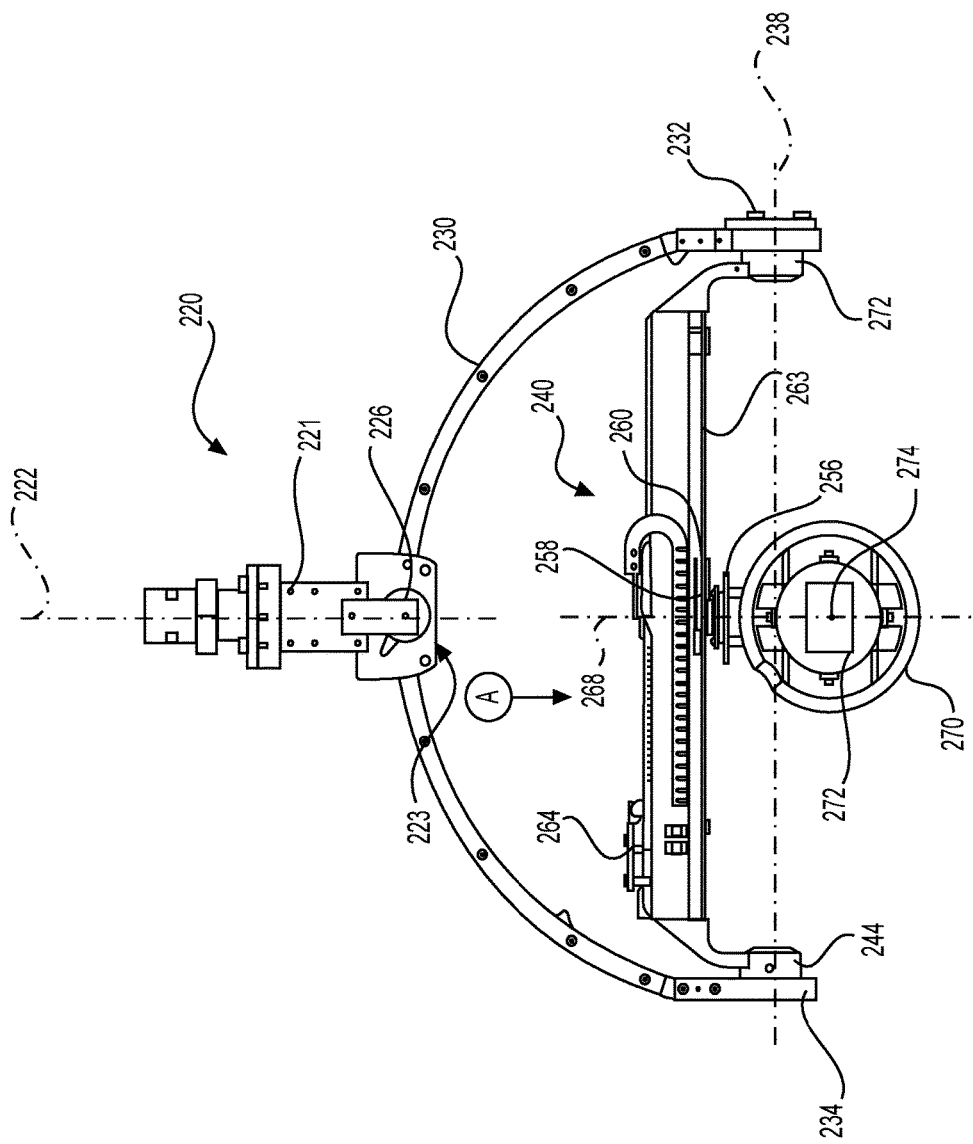
FIG. 4 is a front view of subcomponents of the x-ray source mounting system illustrated in FIG. 2, with housing covers removed, according to an example embodiment herein.
Figure 5:
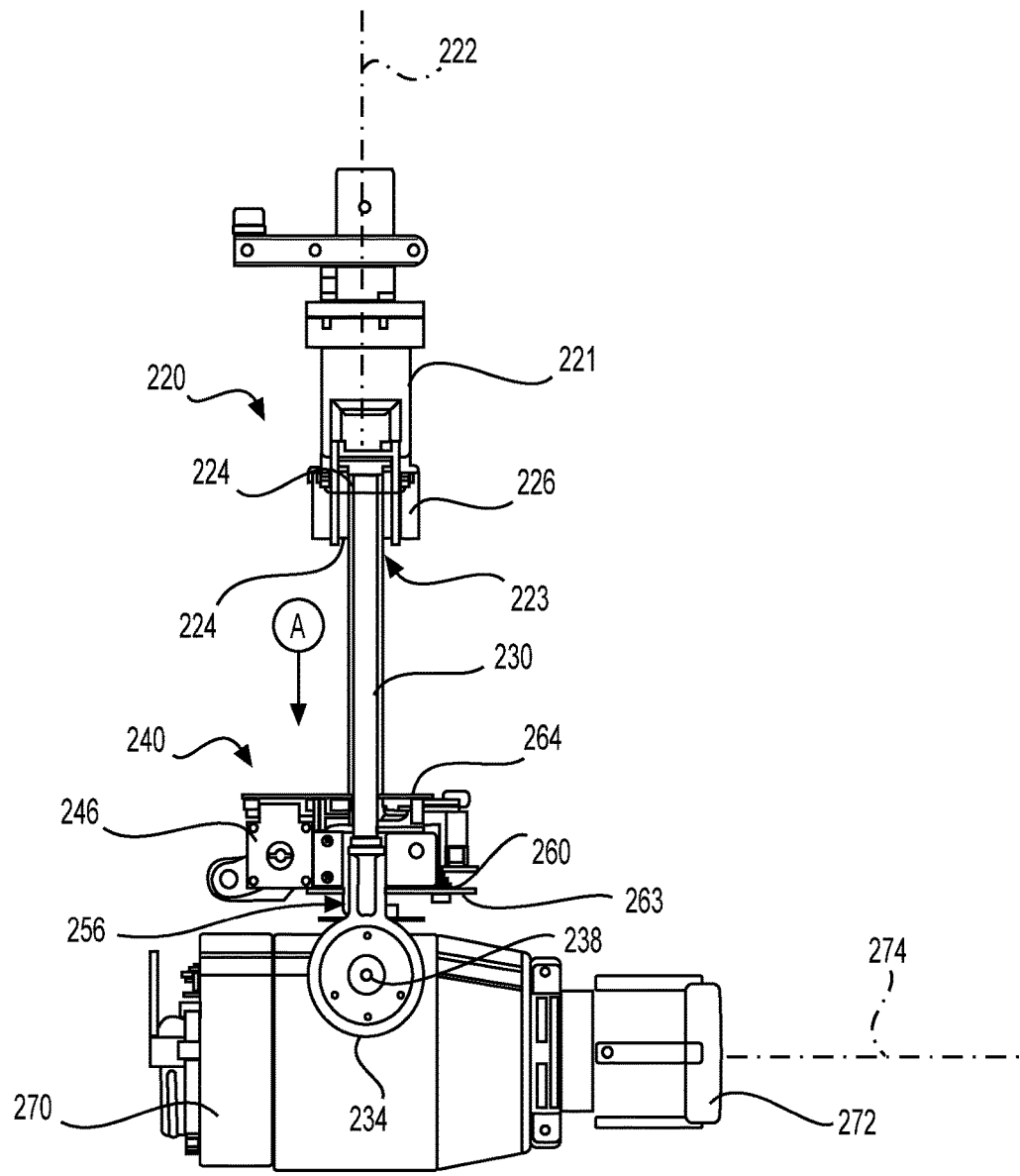
FIG. 5 is a right side view of subcomponents of the x-ray source mounting system illustrated in FIG. 2, with housing covers removed, according to an example embodiment herein.
Figure 6:
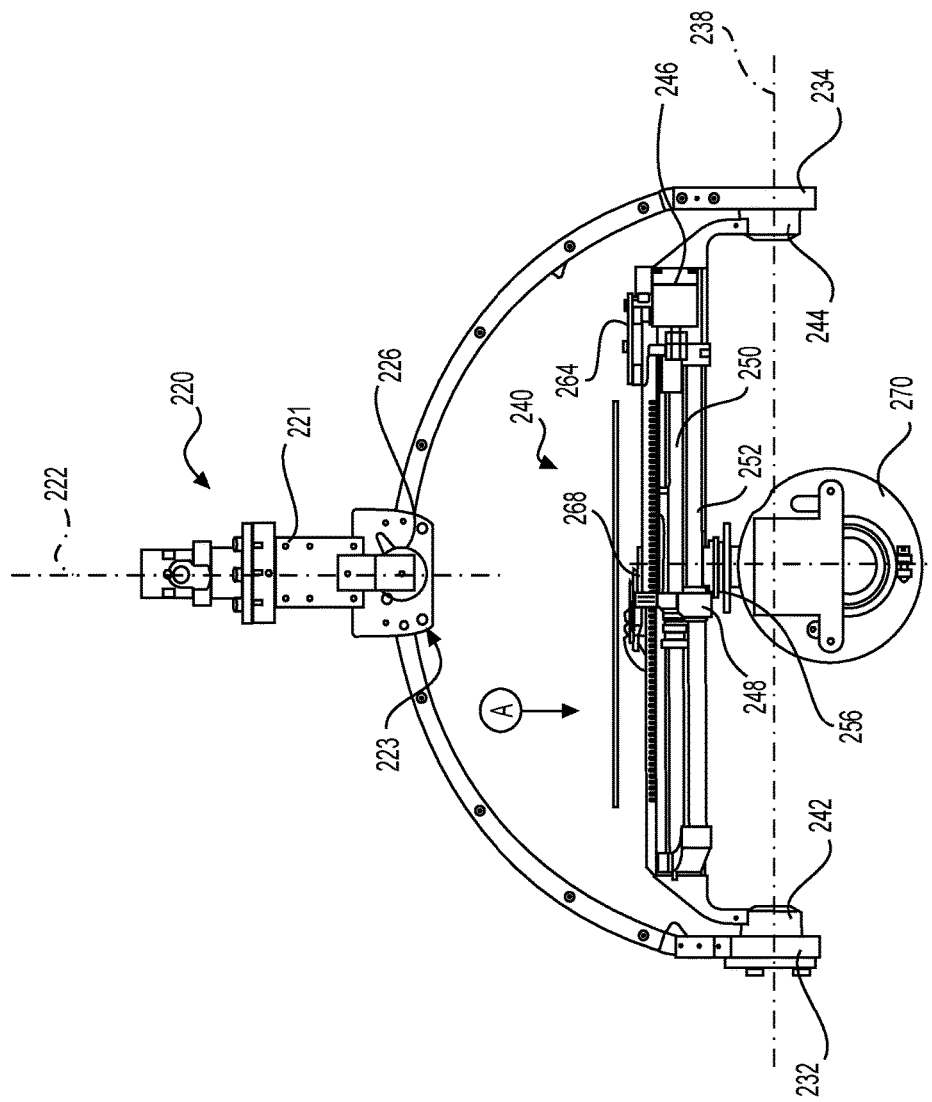
FIG. 6 is a rear view of subcomponents of the x-ray source mounting system illustrated in FIG. 2, with housing covers removed, according to an example embodiment herein.
Figure 7:
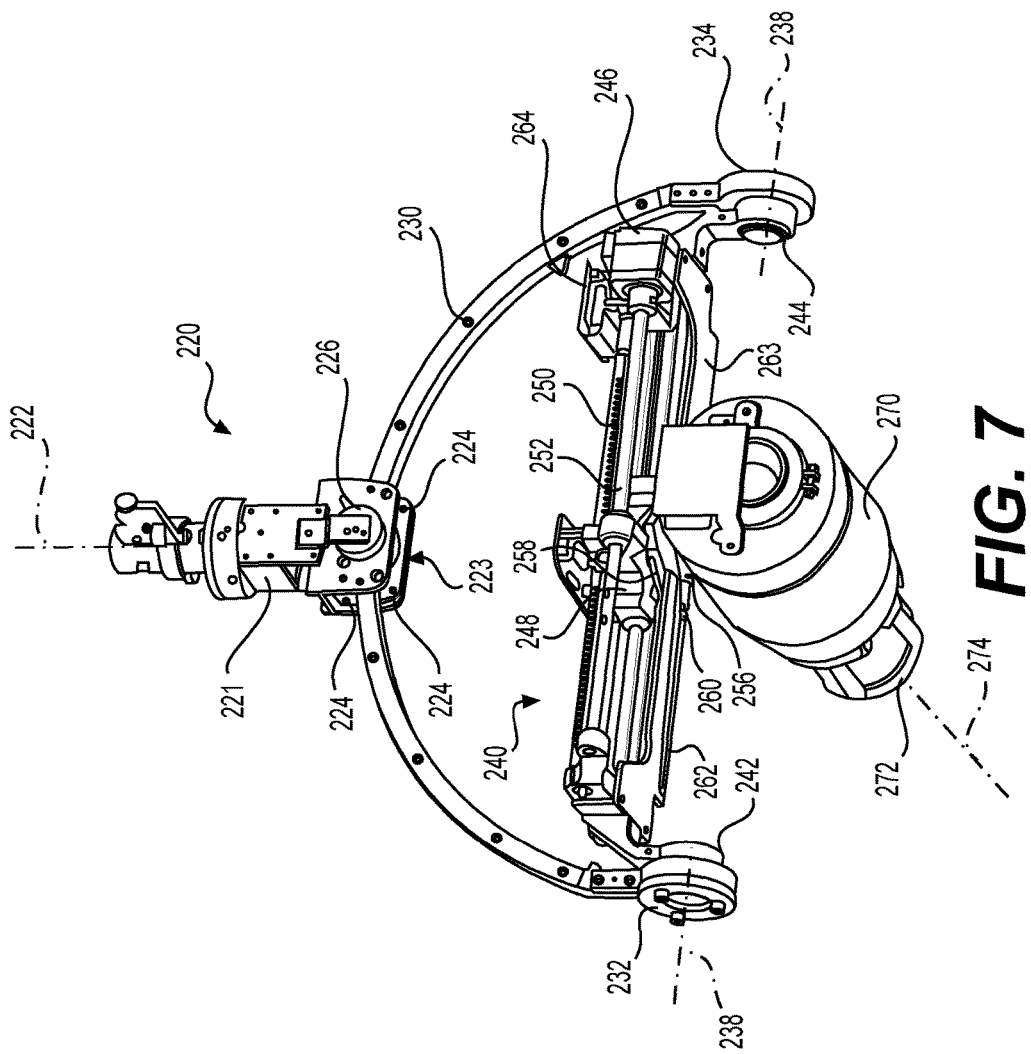
FIG. 7 is a rear-bottom-left perspective view of subcomponents of the x-ray source mounting system illustrated in FIG. 2, with housing covers removed, according to an example embodiment herein.

As described above, the x-ray source 270 attaches to the shaft 256, and translation and rotation of the shaft 256 also is imparted to the x-ray source 270. X-ray source 270 emits x-rays, along an emission axis 274, as shown in FIGS. 9A-9C (in at least some example embodiments herein, the x-ray source 270 also can include a collimator 272 that collimates the emitted x-rays). An aiming position 276 of the x-ray source 270 is defined in a case where the x-ray source 270 is centered between the two arms 242 and 244 of the translation gantry 240 (as illustrated in FIGS. 3A and 9A)

and is oriented such that the emission axis 274 is orthogonal to the translation axis 254 and the pitch axis 238 (as illustrated in FIGS. 3A and 9A) and the emission axis 274 also is parallel to the roll axis 236 (as illustrated in FIG. 3A). For example, the aiming position 276 can be the 0° position in the scan angle 112 discussed above with respect to FIG. 1.

The simultaneous translation and rotation of the shaft 256 discussed above causes the x-ray source 270, by virtue of its attachment to the shaft 256, to sweep a scan angle of ±0° from the aiming position 276, as illustrated in FIGS. 9A-9C. In the above example embodiment, the 40° rotation of the shaft 256 thus causes the x-ray source 270 to sweep a scan angle of ±20° from the aiming position 276.

Although the rotation of the x-ray source 270 can be accomplished by a dedicated motor for rotating the shaft 256 (i.e., a motor independent of the translation motor 246; not shown), such a motor is not necessary, owing to the cam channel 262 and guide pin 260, which rotate the shaft 256 as the x-ray source 270 is translated along translation axis 254 by the translation motor 246. Accordingly, a lower weight, lower cost, and less complex design for sweeping the x-ray source through a scan angle can be realized, as compared to a translation gantry that includes a dedicated motor for rotating the x-ray source 270.

With the x-ray source 270 in the aiming position 276, the operator can precisely and easily aim and align the x-ray source 270 towards an intraoral x-ray sensor 280 included in the mouth of a patient 290, in a manner described further herein below. (The intraoral x-ray sensor 280 of FIG. 2 can serve as the x-ray sensor 102 of FIG. 1). To assist the operator in aiming the x-ray source 270, various reference markers (not shown) can be placed on the x-ray source 270 and/or translation gantry 240 to indicate the aim of the x-ray source 270 with respect to one or more of the yaw axis 222, the pitch axis 238, the roll axis 236, the translation axis 254, and the emission axis 274. Examples of such indicators include a line, a fin, a rib, a graduated scale, a laser projector, and the like, and such indicators can be placed on the housing of the translation gantry 240 or on the x-ray source 270, although these examples are not limiting.

By virtue of the above-described mounting system 200, the position of the x-ray source 270 can be adjusted in six degrees of freedom. The adjustability of the x-ray source 270 will now be described.

The adjustable arm 210 affords the x-ray source 270 with three degrees of translational freedom: the up and down directions, the left and right directions, and the forward and backward directions (other terms also may be used to describe these directions, including but not limited to, a vertical direction, a horizontal direction, an x-direction, a y-direction, or a z-direction).

Figure 10A:
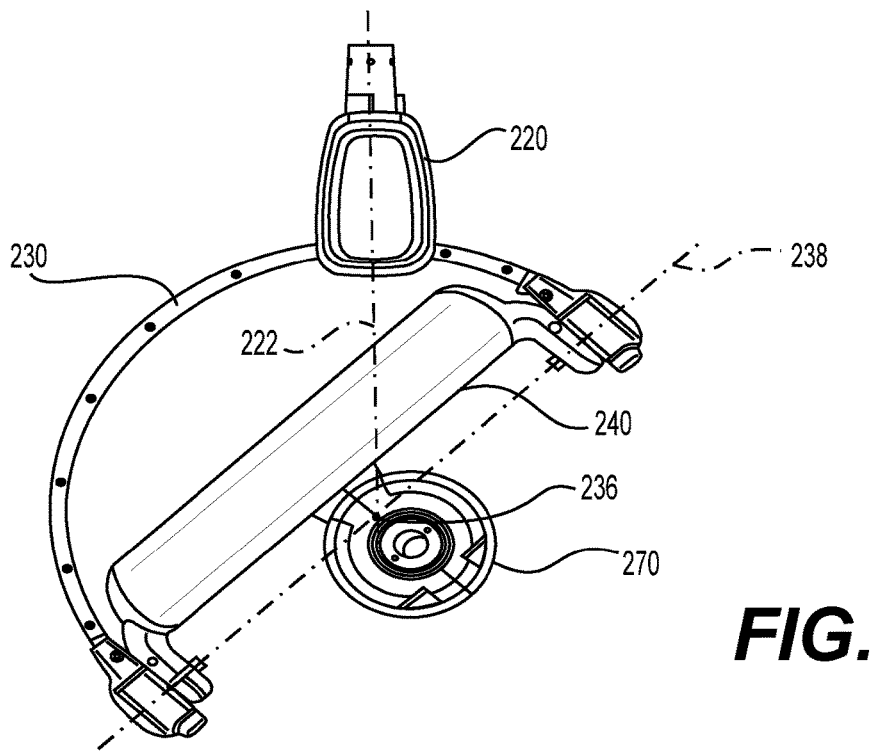
FIG. 10A is a front view of one position of the x-ray source mounting system illustrated in FIG. 2 when rotated about a roll axis.
Figure 10B:
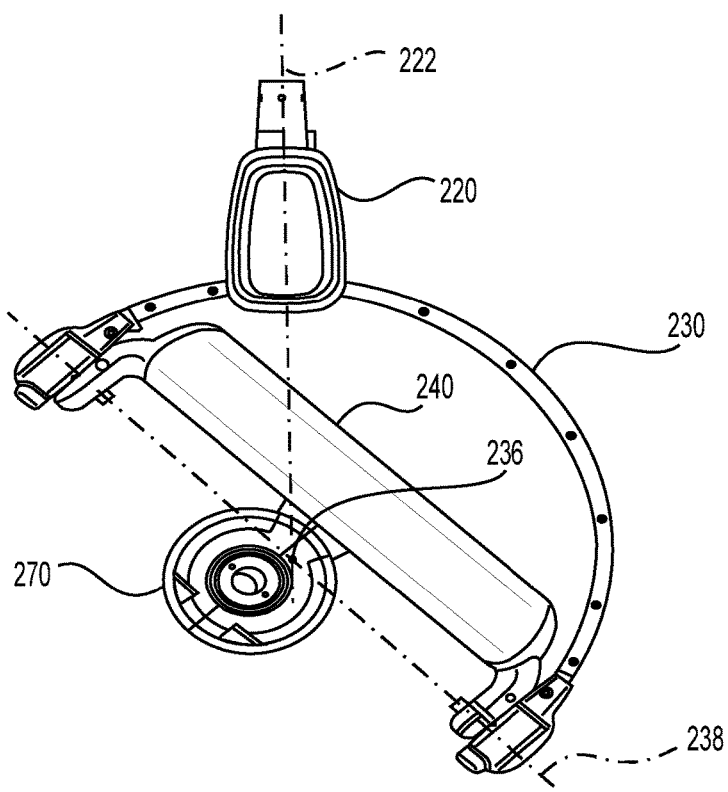
FIG. 10B is a front view of another position of the x-ray source mounting system illustrated in FIG. 2 when rotated about a roll axis.

The mounting system 200 also affords the x-ray source 270 with three degrees of rotational freedom. The swivel 221 of vertical member 220 permits a rotation of the x-ray source 270 around the yaw axis 222 (FIG. 2). Displacing the yoke 230 through the vertical member 220 permits a rotation of the x-ray source 270 substantially around the roll axis 236 (as illustrated in FIGS. 10A and 10B). The x-ray source 270 can be pitched substantially around the pitch axis 238 (FIG. 2) by virtue of the translation gantry arms 242 and 244 forming a pivot with the yoke ends 232 and 234.

In the aiming position 276, the center of mass of the translation gantry 240 and the x-ray source 270 is located in a weight balancing position, that is, the center of mass is substantially coincidental with the intersection of two or more of the yaw axis 222, the roll axis 236, and the pitch axis 238. Accordingly, the yoke 230 acts substantially like a ring of a gyroscope, and rotating the yoke 230 through the vertical member 220 or pitching of the translation gantry 240 does not substantially shift the center of mass. Furthermore, the translation gantry 240 and the x-ray source 270 can be designed to be compact, with mass concentrated close to the intersection of the roll axis 236 and the pitch axis 238 so as to reduce the moment of inertia about each of the roll axis 236 and the pitch axis 238.

By virtue of the balanced and closely concentrated center of mass, the pitch of the translation gantry 240 can be maintained by static frictional forces between the yoke ends 232 and 234 and the corresponding arms 242 and 244 without the assistance of a brake. Also owing to the balanced and concentrated center of mass of the mounting system 200, a user can easily, with minimal force, yaw, pitch, and rotate the x-ray source 270 around the yaw axis 222, pitch axis 238, and the roll axis 236, respectively, to precisely aim and align the x-ray source 270. Accordingly, the x-ray source 270 can be aimed and aligned with an intraoral x-ray sensor 280 placed in a patient's mouth so as to avoid or substantially minimize cone cut in at least a substantial majority of the images acquired throughout the scan angle.

In one example embodiment herein, the x-ray source 270 and the translation gantry 240 (more particularly, the motor 246) are in communication with and can be controlled by a computer system 106 illustrated in FIG. 1. For example, the x-ray source 270 can be controlled to emit x-rays and the translation gantry 240 can be controlled to translate the x-ray source 270 in the manner described above. In some other example embodiments herein, the translation gantry 240 can include one or more on-board controller(s) 264 (as shown in, for example, FIGS. 3A-3D) that function(s) to control, at least in part, the motor 246 and/or the x-ray source 270. In some example embodiments herein, the controller 264 can serve as the motor controller 120 illustrated in FIG. 1. These examples are merely illustrative in nature, and in other embodiments, different degrees of control can be distributed between the computer system 106 and on-board controllers 264.

Computer System

Figure 11:
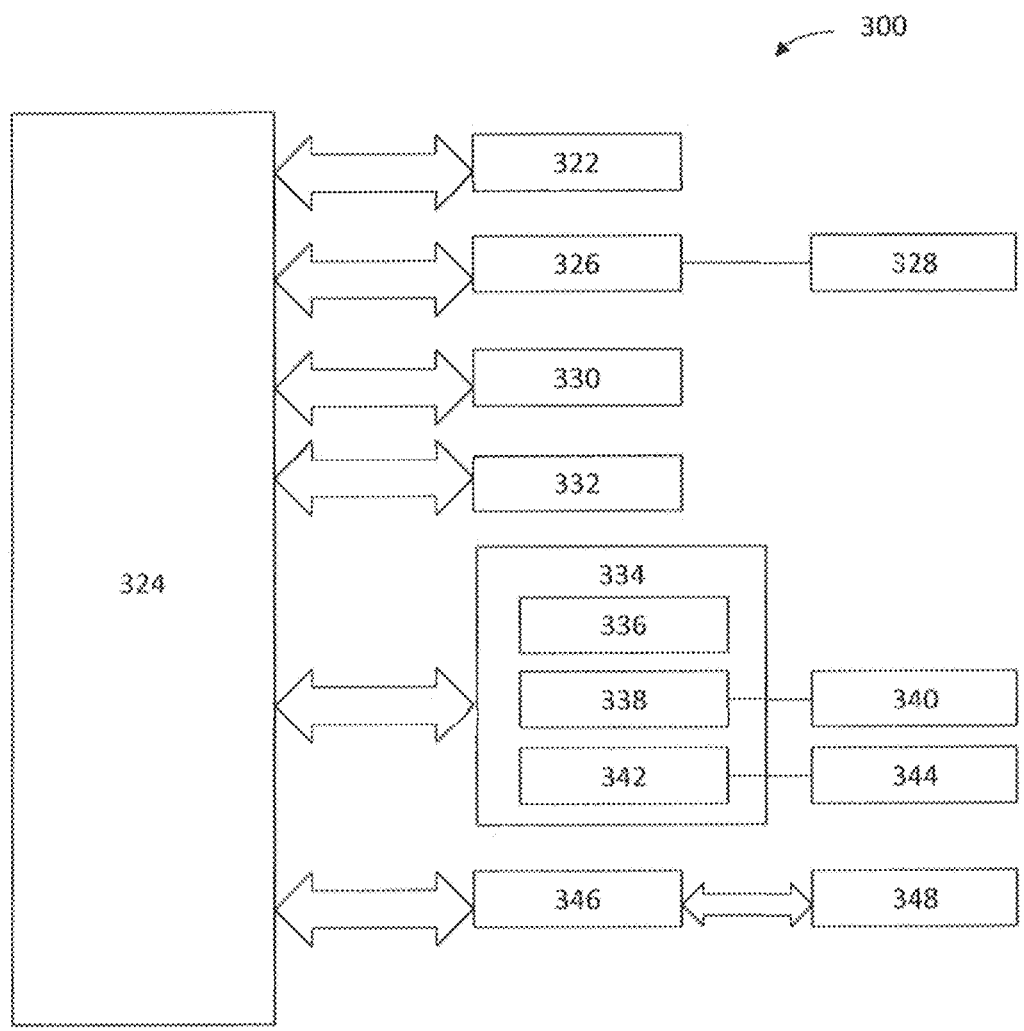
FIG. 11 illustrates a block diagram of an example computer system of the tomosynthesis system shown in FIG. 1.

FIG. 11 illustrates a block diagram of a computer system 300. In one example embodiment herein, at least some components of the computer system 300 (such as all those components, or all besides display unit 328) can form or be included in the computer system 106 shown in FIG. 1. The computer system 300 includes at least one computer processor 322 (also referred to as a "controller"). The computer processor 322 may include, for example, a central processing unit, a multiple processing unit, an application-specific integrated circuit ("ASIC"), a field programmable gate array ("FPGA"), or the like. The processor 322 is connected to a communication infrastructure 324 (e.g., a communications bus, a cross-over bar device, or a network).

The computer system 300 also includes a display interface (or other output interface) 326 that forwards video graphics, text, and other data from the communication infrastructure 324 for display on a display unit 328 (which, in one example embodiment, can form or be included in the display unit 108).

The computer system 300 also includes an input unit 330 that can be used by a user of the computer system 300 to send information to the computer processor 322. In one example embodiment herein, the input unit 330 can form or be included in the input unit 114. For example, the input unit 330 can include a keyboard device and/or a mouse device or other input device. In one example, the display unit 328, the input unit 330, and the computer processor 322 can collectively form a user interface.

In an example embodiment that includes a touch screen, for example, the input unit 330 and the display unit 328 can be combined, or represent a same user interface. In such an embodiment, a user touching the display unit 328 can cause corresponding signals to be sent from the display unit 328 to the display interface 326, which can forward those signals to a processor such as processor 322, for example.

In addition, the computer system 300 includes a main memory 332, which preferably is a random access memory ("RAM"), and also may include a secondary memory 334. The secondary memory 334 can include, for example, a hard disk drive 336 and/or a removable-storage drive 338 (e.g., a floppy disk drive, a magnetic tape drive, an optical disk drive, a flash memory drive, and the like). The removable-storage drive 338 reads from and/or writes to a removable storage unit 340 in a well-known manner. The removable storage unit 340 may be, for example, a floppy disk, a magnetic tape, an optical disk, a flash memory device, and the like, which is written to and read from by the removable-storage drive 338. The removable storage unit 340 can include a non-transitory computer-readable storage medium storing computer-executable software instructions and/or data.

In alternative embodiments, the secondary memory 334 can include other computer-readable media storing computer-executable programs or other instructions to be loaded into the computer system 300. Such devices can include a removable storage unit 344 and an interface 342 (e.g., a program cartridge and a cartridge interface similar to those used with video game systems); a removable memory chip (e.g., an erasable programmable read-only memory ("EPROM") or a programmable read-only memory ("PROM")) and an associated memory socket; and other removable storage units 344 and interfaces 342 that allow software and data to be transferred from the removable storage unit 344 to other parts of the computer system 300.

The computer system 300 also can include a communications interface 346 that enables software and data to be transferred between the computer system 300 and external devices. Examples of the communications interface 346 include a modem, a network interface (e.g., an Ethernet card or an IEEE 802.11 wireless LAN interface), a communications port (e.g., a Universal Serial Bus ("USB") port or a FireWire® port), a Personal Computer Memory Card International Association ("PCMCIA") interface, and the like. Software and data transferred via the communications interface 346 can be in the form of signals, which can be electronic, electromagnetic, optical or another type of signal that is capable of being transmitted and/or received by the communications interface 346. Signals are provided to the communications interface 346 via a communications path 348 (e.g., a channel). The communications path 348 carries signals and can be implemented using wire or cable, fiber optics, a telephone line, a cellular link, a radio-frequency ("RF") link, or the like. The communications interface 346 also may be used to transfer software or data or other information between the computer system 300 and a remote server or cloud-based storage (not shown).

One or more computer programs (also referred to as computer control logic) are stored in the main memory 332 and/or the secondary memory 334. The computer programs also can be received via the communications interface 346. The computer programs include computer-executable instructions which, when executed by the computer processor 322, cause the computer system 300 to perform the procedures as described herein. Accordingly, the computer programs can control the computer system 106 and other components (e.g., the x-ray sensor 102 and the x-ray source 104) of the tomosynthesis system 100.

In one example embodiment herein, the software can be stored in a non-transistory computer-readable storage medium and loaded into the main memory 332 and/or the secondary memory 334 of the computer system 300 using the removable-storage drive 338, the hard disk drive 336, and/or the communications interface 346. Control logic (software), when executed by the processor 322, causes the computer system 300, and more generally the intraoral tomosynthesis system 100, to perform the procedures described herein.

In another example embodiment hardware components such as ASICs, FPGAs, and the like, can be used to carry out the functionality described herein. Implementation of such a hardware arrangement so as to perform the functions described herein will be apparent to persons skilled in the relevant art(s) in view of this description.

Method of Imaging with an Adjustable X-Ray Source Mounting System

Figure 12:
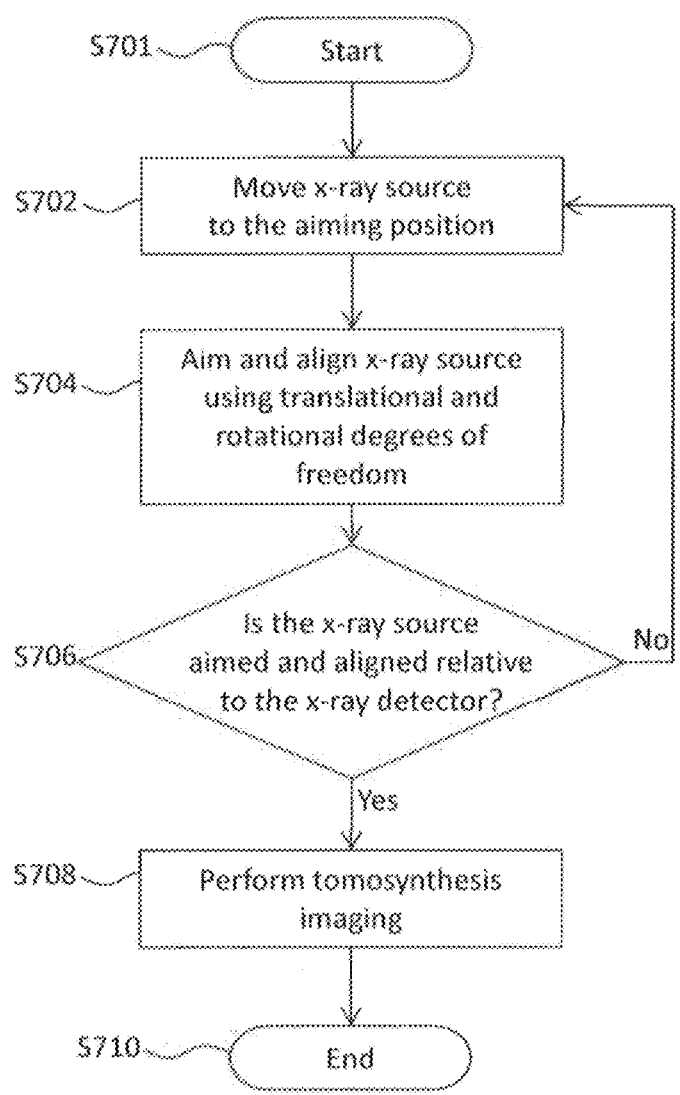
FIG. 12 is a flowchart illustrating a procedure according to an example embodiment herein for positioning an x-ray source using the x-ray source mounting system of FIG. 2.

A method of tomosynthesis imaging using the intraoral tomosynthesis system 100 (FIG. 1), which includes the x-ray source 270 mounted to the adjustable mounting system 200 and the intraoral x-ray sensor 280, (FIG. 2) will now be described with reference to FIG. 12, which is a flowchart showing one example embodiment of the method.

Prior to positioning the x-ray source 270, a patient 290 is seated in dental chair (not shown), which can be adjusted for the patient's comfort, and an intraoral x-ray sensor 280 is placed in the patient's mouth. In some example embodiments herein, the intraoral x-ray sensor 280 can be a rectangular Size-0, Size-1, or Size-2 sensor, as described above, and also can be attached to an extraoral guide 282, which provides a target for aiming and aligning the x-ray source 270.

The process starts at Step S701, and in step S702, the operator commands the computer system 106 via input unit 114 to control the translation gantry 240 to move the x-ray source 270 along the translation axis 254 to the aiming position 276.

In step S704, the operator manually moves and/or rotates the x-ray source 270 by way of the mounting system 200 in one or more of the degrees of freedom described above (i.e., up/down translation, left/right translation, forward/backward translation, yaw rotation, pitch rotation, and roll rotation) to aim and align the x-ray source 270 with the intraoral x-ray sensor 280 (or with the extraoral guide 282, if applicable).

In one example embodiment, herein, a method and device for aiming and aligning the x-ray source 270 relative to the intraoral x-ray sensor 280 can be accomplished through a dental positioning system, such as that described in U.S. patent Ser. No. 13/591,979, which is incorporated by reference herein in its entirety, as if set forth fully herein.

In decision block S706, the operator checks the aim and alignment of the x-ray source 270 relative to the intraoral x-ray sensor 280. The x-ray source 270 is deemed to be properly aimed and aligned if the emission axis 274 projects orthogonally on to the intraoral x-ray sensor 280 substantially close to the sensor's center, and the x-rays emitted by the x-ray source 270 at each position in the scan angle 112 would be received at the intraoral x-ray sensor 280 without cone cut. In particular, if the intraoral sensor 280 is rectangular, it may be useful to rotate the yoke 230 such that the translation axis 254 is parallel to one of the rectangular axes of the intraoral x-ray sensor 280 (e.g., the long rectangular axis, in particular).

If the x-ray source 270 is deemed in decision block S706 to be not properly aimed and aligned, then the operator again performs steps S702 and/or S704 to reposition the x-ray source 270 and, subsequently, again performs decision block S706 to check the aim and alignment of the x-ray source 270.

If the x-ray source 270 is deemed in decision block S706 to be aimed and aligned properly, then the process proceeds to step S708.

In step S708, the intraoral tomosynthesis system 100 (FIG. 1) is controlled to acquire a plurality of projection images of object 50 (e.g., at least part of the patient's dental anatomy) over a scan angle 112, including the orthogonal projection image (i.e., the image acquired with the x-ray source 270 at 0° in the scan angle 112, which also is the aiming position 276), in the manner described above.

For example, and as described above, the translation motor 246 is controlled by the computer system 106 and/or the controller 264 to translate the x-ray source 270 along the translation axis, which also causes the x-ray source 270 to rotate through the scan angle 112 by virtue of the cam system. Simultaneous to the translation, the x-ray source 270 is controlled by computer system 106 and/or the controller 264 to emit x-rays along the emission axis 274 through object 50, and the intraoral x-ray sensor 280 converts x-rays received at its receiving surface into electrical signals that are then transmitted to computer system 106. The computer system 106 processes the electrical signals to acquire a plurality of 2D projection images, and then further processes the plurality of projection images to reconstruct a series of tomographic image slices.

The process ends at Step S710.

In view of the foregoing description, it can be appreciated that one or more of the example embodiments described herein relate to a compact and lightweight tomosynthesis-capable x-ray source mounting system that allows an operator to precisely and effortlessly aim an x-ray source using multiple degrees of freedom. Because the x-ray source mount system is highly maneuverable, compact, and lightweight, dental clinicians can equip an advanced tomosynthesis-based 3D imaging system for chair-side imaging without sacrificing suite space (in contrast to large footprint CT machines). Additionally, the x-ray source mounting system can be used to perform both tomosynthesis imaging (by sweeping the x-ray source through a limited scan angle) and standard digital radiography (by imaging without sweeping the x-ray source), and thus can replace a clinician's existing dental radiography x-ray source.

The various embodiments described above have been presented by way of example and not limitation. It will be apparent to persons skilled in the relevant art(s) that various changes in form and detail can be made therein without departing from the spirit and scope of the present invention. Thus, the present invention should not be limited by any of the above-described exemplary embodiments, but should be defined only in accordance with the following claims and their equivalents.

In addition, it should be understood that the attached drawings, which highlight functionality described herein, are presented as illustrative examples. The architecture of the present invention is sufficiently flexible and configurable, such that it can be utilized and navigated in ways other than that shown in the drawings.

Moreover, the example embodiments described herein are not limited to intraoral tomosynthesis imaging. The example embodiments described herein can be used to perform scans of other anatomical regions.

Further, the purpose of the Abstract is to enable the U.S. Patent and Trademark Office and the public generally, and especially scientists, engineers, and practitioners in the relevant art(s), who are not familiar with patent or legal terms and/or phraseology, to determine quickly from a cursory inspection the nature and essence of the technical subject matter disclosed herein. The Abstract is not intended to be limiting as to the scope of the present invention in any way. It is also to be understood that the procedures recited in the claims need not be performed in the order presented.

What is claimed is:

1. An adjustable mount for positioning an x-ray source, the adjustable mount comprising:
    a vertical member configured to swivel around a yaw axis defined by the vertical member;
    a circular arc-shaped yoke having two ends, the circular arc-shaped yoke passing through a channel of the vertical member,
        wherein a pitch axis is defined through the two ends of the yoke, and
        wherein a roll axis is defined through a circle center of the yoke and orthogonally to a plane in which the yoke lies;
    a gantry attached to the two ends of the yoke, wherein the gantry is constructed to pitch about the pitch axis; and
    an x-ray source attached to the gantry,
    wherein the x-ray source is configured to (i) rotate around the yaw axis by swiveling the vertical member, (ii) pitch around the pitch axis by pitching the gantry, or (iii) rotate around the roll axis by moving the yoke through the channel of the vertical member.

2. The adjustable mount of claim 1, wherein the gantry includes a motorized translation stage, and wherein the x-ray source is attached to the gantry by way of the translation stage.

3. The adjustable mount of claim 2, wherein the gantry includes a cam channel configured to rotate the x-ray source based on a translation of the x-ray source by the translation stage.

4. The adjustable mount of claim 2, wherein the motorized translation stage includes a lead screw.

5. The adjustable mount of claim 1, wherein the vertical member includes bearings on which the yoke rolls and a brake to clamp the yoke.

6. The adjustable mount of claim 1, wherein the yoke is a circular arc.

7. The adjustable mount of claim 1, wherein the vertical member is suspended from an adjustable arm.

8. The adjustable mount of claim 1, wherein the x-ray source and the gantry are configured to allow the x-ray source to translate along a translation axis substantially parallel to the pitch axis while rotating about the yaw axis.

9. The adjustable mount of claim 8, wherein the x-ray source and the gantry are configured to allow the x-ray source to rotate through a predetermined scan angle.

10. The adjustable mount of claim 9, wherein the predetermined scan angle is ±20° from an aiming position.

11. An x-ray imaging system comprising:
    an adjustable mount, including:
        a vertical member configured to swivel around a yaw axis defined by the vertical member, a circular arc-shaped yoke having two ends, the circular arc-shaped yoke passing through a channel of the vertical member,
wherein a pitch axis is defined through the two ends of the yoke, and
wherein a roll axis is defined through a circle center of the yoke and orthogonally to a plane in which the yoke lies, and
a gantry attached to the two ends of the yoke, wherein the gantry is arranged to pitch about the pitch axis;
an x-ray source attached to the gantry of the adjustable mount; and
an x-ray sensor,
wherein the x-ray source is configured to be aimed at the x-ray sensor by at least one of (i) rotating around the yaw axis by swiveling the vertical member, (ii) pitching around the pitch axis by pitching the gantry, and (iii) rotating around the roll axis by passing the yoke through the vertical member.

12. A method of x-ray imaging with an x-ray imaging system, the x-ray imaging system includes an adjustable mounting system that includes a translation gantry to which an x-ray source is attached, wherein the adjustable mounting system permits rotation of the x-ray source around a yaw axis, a pitch axis, and a roll axis, the method comprising:
performing a scanning operation of translating the x-ray source along a translation axis of the translation gantry that is substantially parallel to the pitch axis while rotating the x-ray source about the yaw axis,
wherein x-rays are emitted from the x-ray source during the scanning operation.

13. The method of claim 12, further comprising:
centering the x-ray source at an aiming position; and
aiming the centered x-ray source at an x-ray sensor by rotating the x-ray source about a roll axis of the adjustable mounting system.

14. The method of claim 12, further comprising:
detecting the emitted x-rays at an x-ray sensor,
wherein the x-ray source is rotated through a predetermined scan angle during the scanning operation.

15. An x-ray source mounting system, comprising:
an x-ray source; and
an adjustable mounting system that includes a translation gantry to which the x-ray source is attached, the adjustable mounting system is configured to provide the x-ray source with rotational degrees of freedom about a yaw axis, a pitch axis, and a roll axis,
wherein the x-ray source and the translation gantry are configured to allow the x-ray source to translate along a translation axis substantially parallel to the pitch axis while the x-ray source rotates about the yaw axis.

16. The x-ray source mounting system according to claim 15, wherein a center of mass of the x-ray source and the translation gantry does not shift when the x-ray source is rotated around at least one of a yaw axis, a pitch axis, and a roll axis.

* * * * *